(12) United States Patent
Antelman et al.

(10) Patent No.: US 9,901,541 B2
(45) Date of Patent: Feb. 27, 2018

(54) TOPICAL ANTIBIOTIC FORMULATIONS

(71) Applicant: AIDANCE SKINCARE & TOPICAL SOLUTIONS LLC, Woonsocket, RI (US)

(72) Inventors: Perry Antelman, Sharon, MA (US); Bharat Madhavan, Kingston, RI (US); Joshua Steven Stein, Sharon, MA (US); Elia Altabet, Sharon, MA (US); Shalom Lampert, Maalot (IL)

(73) Assignee: AIDANCE SKINCARE & TOPICAL SOLUTIONS LLC, Woonsocket, RI (US)

( * ) Notice: Subject to any disclaimer, the term of this patent is extended or adjusted under 35 U.S.C. 154(b) by 0 days.

(21) Appl. No.: 15/064,623

(22) Filed: Mar. 9, 2016

(65) Prior Publication Data

US 2016/0184221 A1    Jun. 30, 2016

Related U.S. Application Data

(63) Continuation of application No. PCT/IB2015/050630, filed on Jan. 27, 2015.

(60) Provisional application No. 61/931,944, filed on Jan. 27, 2014.

(51) Int. Cl.
| | |
|---|---|
| *A61K 33/38* | (2006.01) |
| *A61K 9/10* | (2006.01) |
| *A61K 9/06* | (2006.01) |
| *A61K 9/00* | (2006.01) |

(52) U.S. Cl.
CPC .............. *A61K 9/0014* (2013.01); *A61K 9/06* (2013.01); *A61K 9/10* (2013.01); *A61K 33/38* (2013.01)

(58) Field of Classification Search
CPC .......... A61K 9/0014; A61K 9/10; A61K 9/06; A61K 33/38
See application file for complete search history.

(56) References Cited

U.S. PATENT DOCUMENTS

2003/0072810 A1*   4/2003   Burrell ................ A61K 9/0014
                                                                424/618

FOREIGN PATENT DOCUMENTS

EP          0 255 248      *   2/1988

OTHER PUBLICATIONS

CN 101336640 A "Tetrasilver tetroxide bactericide, preparation method and use thereof," Eng. Trans, Jan. 2009.*
Kazachenko et al. "Synthesis and Antimicrobial Activity of Silver Complexes With Histidine and Tryptophan" in Pharmaceutical Chemistry Journal, vol. 34, No. 5, May 200, pp. 34 and 35.*
Dellasega, "Nanostructured Silver oxide film with enhanced antibacterial activity" in Nanotechnology 19 (2008), 6 pages.*

* cited by examiner

*Primary Examiner* — Blessing M Fubara
(74) *Attorney, Agent, or Firm* — Daniel Feigelson; Fourth Dimension IP

(57) ABSTRACT

There are disclosed topical silver(II) antibiotic formulations. Other embodiments are also disclosed.

25 Claims, 13 Drawing Sheets

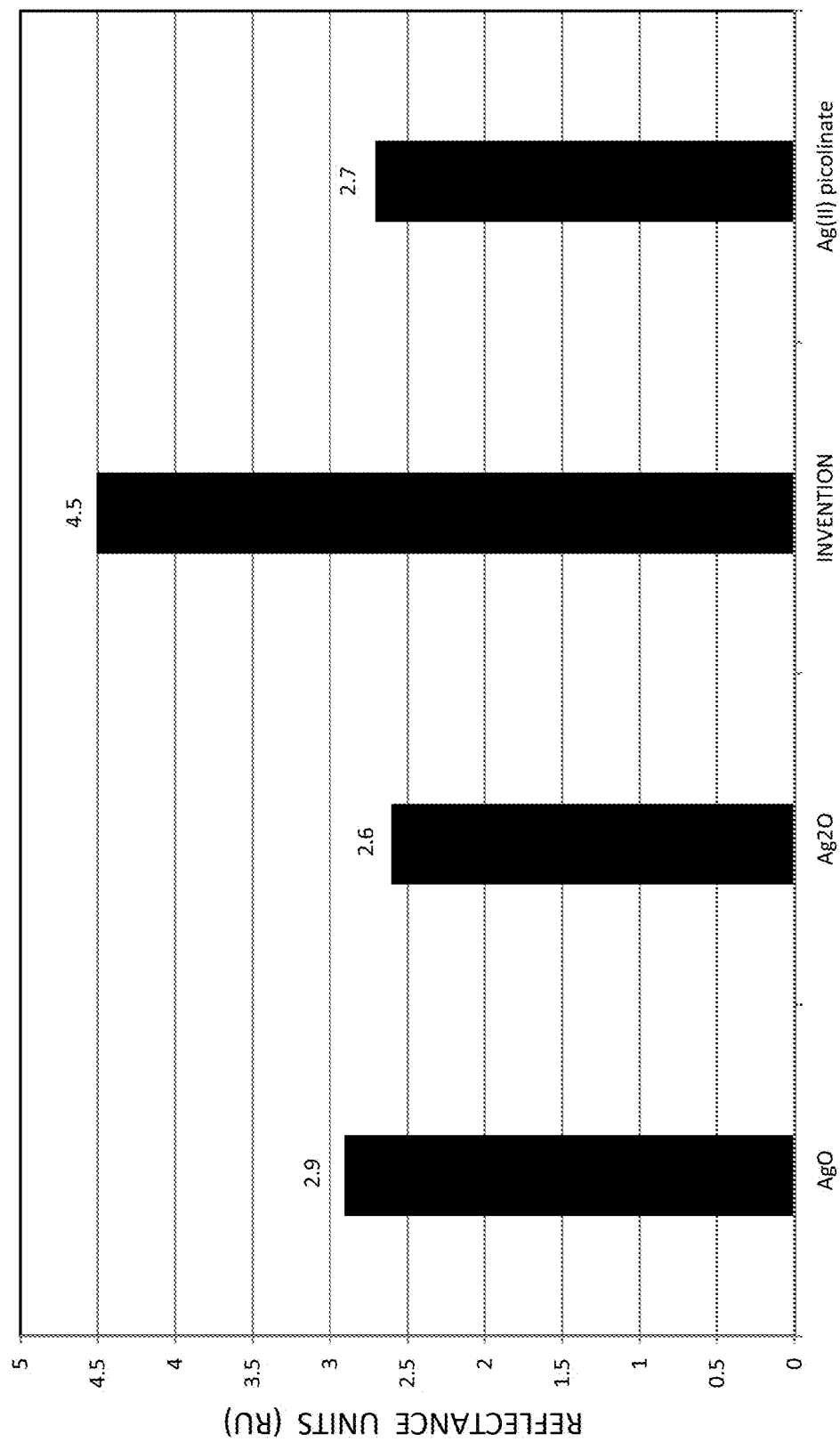

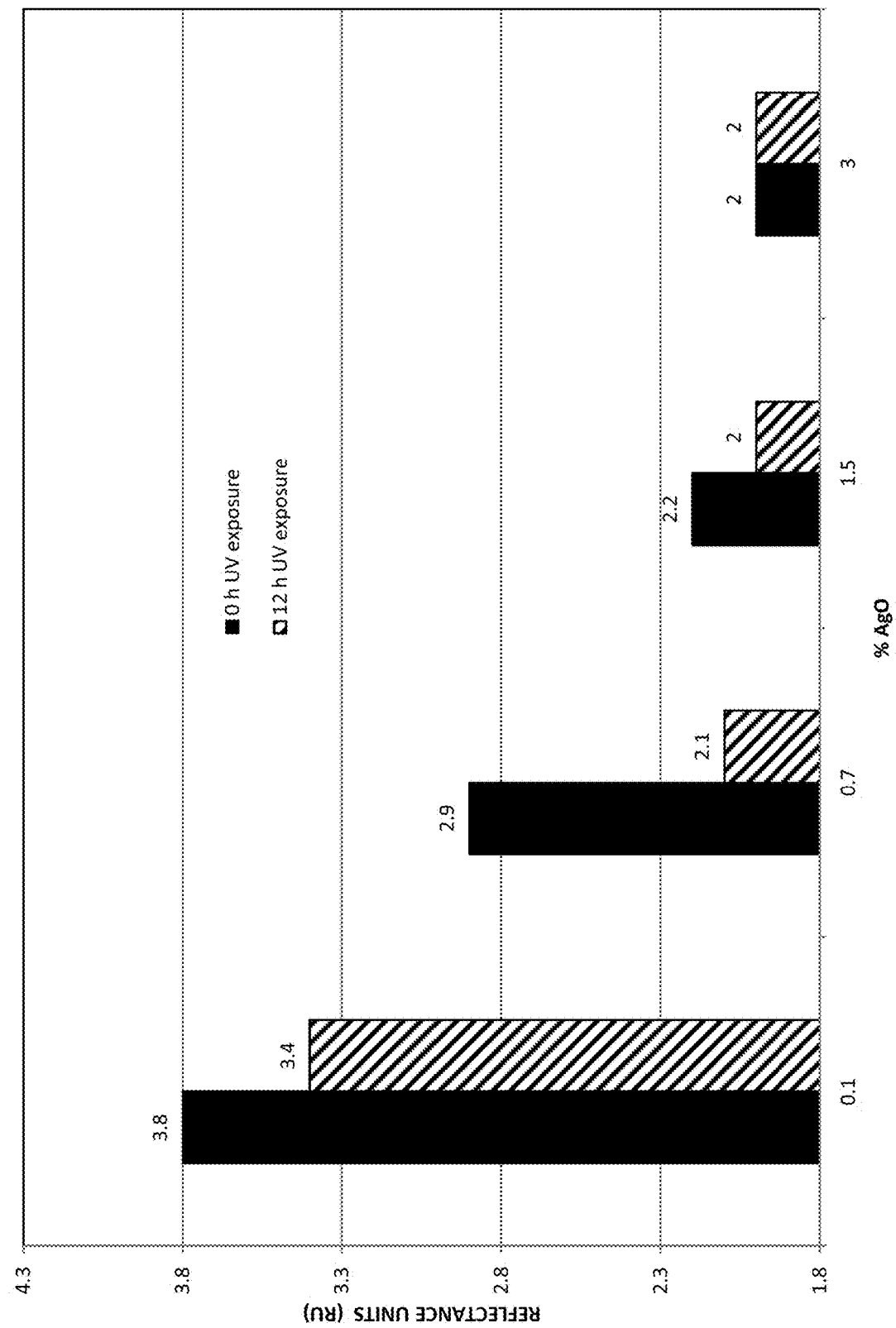

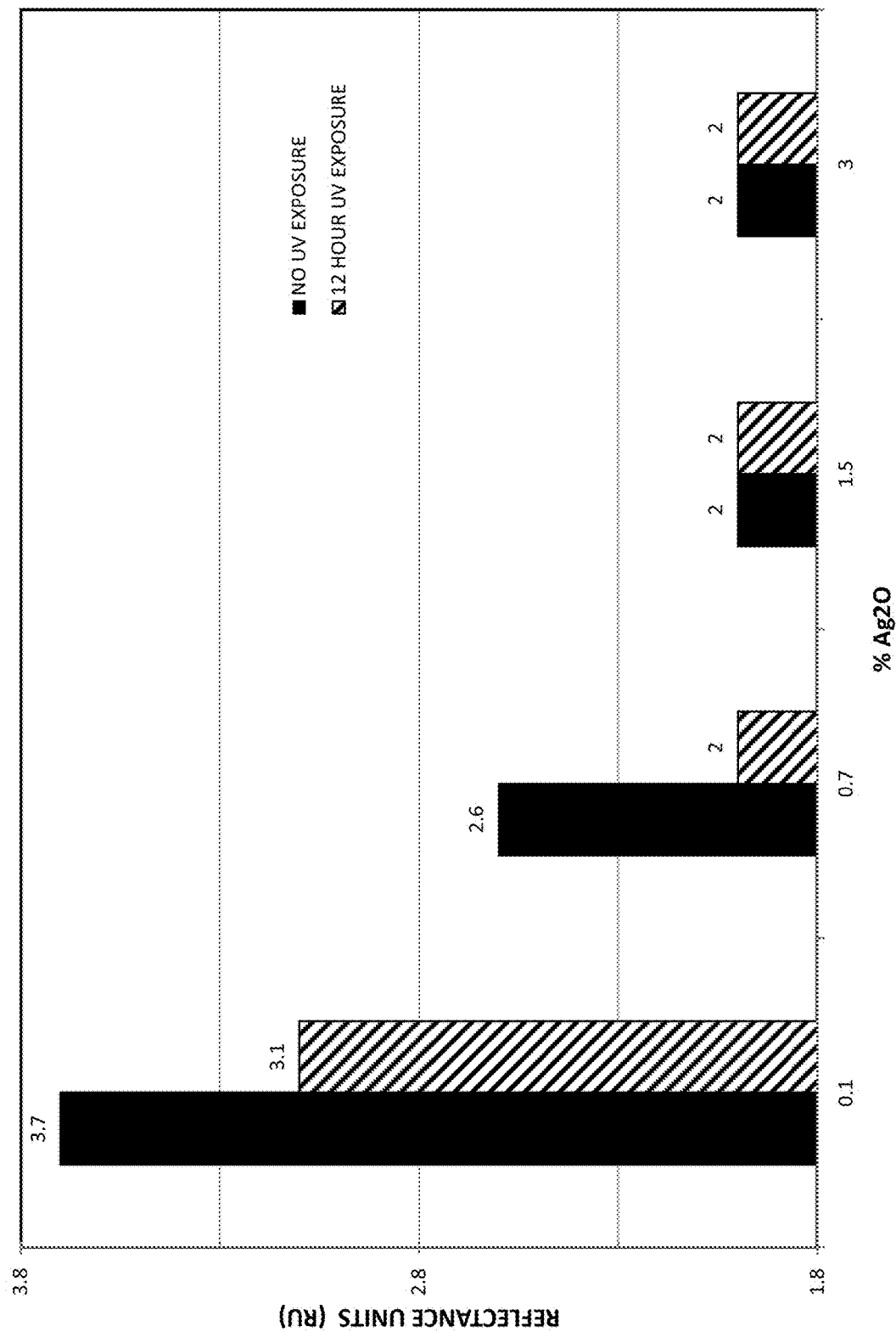
FIGURE 10 -- PRIOR ART

TOPICAL ANTIBIOTIC FORMULATIONS

This application is a continuation of PCT/IB2015/050630, filed Jan. 27, 2015, which claims the benefit of Provisional Application Ser. No. 61/931,944, filed Jan. 27, 2014. Said applications are incorporated herein by reference for all purposes as if fully set forth herein.

FIELD AND BACKGROUND OF THE INVENTION

The present invention relates to antibiotic formulations and methods, and more particularly, to topical silver(II) antibiotic formulations, methods of production thereof, and methods of use thereof.

While substantial advances have been made in the treatment of topical wounds, both chronic and acute, the inventors believe there is a need for further improvements in formulating stable, efficacious topical antibiotic formulations and medical devices; the subject matter of the present disclosure and claims is aimed at fulfilling this need.

SUMMARY OF THE INVENTION

According to teachings of the present invention there is provided an antimicrobial formulation including: (a) at least one silver-containing compound, including an anti-microbial agent containing an aliphatic silver carboxylate, the silver of the aliphatic silver carboxylate having a nominal valence of 2, the at least one silver-containing compound having an average valence of at least 1.1; and (b) a carrier base; the at least one silver-containing compound being dispersed within the base.

According to an aspect of the present invention there is provided an antimicrobial formulation suitable for application to skin tissue, the formulation including: (a) at least one silver-containing compound including at least one silver carboxylate, the silver of the carboxylate having a nominal valence of 2 or at least 2, the at least one silver-containing compound having an average valence of at least 1.1; and (b) a carrier base; the at least one silver-containing compound being intimately dispersed within the base, the formulation having a standard whiteness value of at least 4.0, at least 4.1, at least 4.2, or at least 4.3 reflective units (RU); the formulation having a total silver concentration of at least 0.10%, at least 0.20%, at least 0.30%, at least 0.50%, at least 0.70%, at least 1.00%, at least 1.5%, at least 2.0%, at least 2.5%, or at least 3.0%.

According to an aspect of the present invention there is provided an antimicrobial formulation suitable for use in topical applications to skin tissue, the formulation including at least one silver-containing compound, including an anti-microbial agent containing at least one silver carboxylate, the silver of the carboxylate having a nominal valence of at least 2, the at least one silver-containing compound having an average valence of at least 1.1.

According to an aspect of the present invention there is provided a use of a silver carboxylate in the manufacture of a medicament for the treatment of a topical condition, the silver of the silver carboxylate having a nominal valence of at least 1.1, at least 1.2, at least 1.3, at least 1.4, at least 1.5, at least 1.6, at least 1.7, at least 1.8, at least 1.9, or 2.0 or substantially 2.0.

According to an aspect of the present invention there is provided an antimicrobial formulation suitable for application to skin tissue, the formulation including: (a) at least one silver-containing compound, including an anti-microbial agent containing at least one silver carboxylate, the silver of the silver carboxylate having a nominal valence of at least 1.1; and (b) a carrier base.

According to an aspect of the present invention there is provided a method of producing a silver(II) carboxylate or silver(II) carboxylate formulation, the method including the steps of: (a) mixing the carboxylic acid and the silver(II) oxide to produce a reaction mixture; and (b) heating the reaction mixture to produce an aliphatic silver carboxylate, the silver of the aliphatic silver carboxylate having a nominal valence of 2.

The reaction mixture obtained, or the silver(II) carboxylate therein, may be mixed with a carrier base to produce the silver(II) carboxylate formulation.

The reaction temperature may be at least 50° C., at least 60° C., or at least 70° C., and more typically, at least 80° C., at least 84° C., or at least 86° C. The reaction temperature may be at most 135° C., at most 125° C., at most 115° C., at most 110° C., at most 107° C., at most 105° C., at most 103° C., at most 100° C., at most 98° C., at most 96° C., or at most 94° C. The reaction temperature may be within a range of 60° C. to 110° C., 80° C. to 110° C., 80° C. to 105° C., 84° C. to 105° C., 84° C. to 100° C., 84° C. to 98° C., 84° C. to 96° C., or 86° C. to 96° C.

The reaction mixture may be agitated for at least a portion of step (b), and more typically, substantially throughout step (b).

The carboxylic acid may be pre-heated, as necessary, prior to the mixing with the silver(II) oxide. Typically, the carboxylic acid is brought to liquid form prior to this mixing.

A solvent or solvents may be introduced to form a portion of the reaction mixture. Preferably, any such solvents should be impervious or largely impervious to oxidation by the silver(II) oxide, and may be selected to at least partially dissolve the carboxylic acid.

The heating may be curtailed after a lightening of the reaction mixture. The lightening may be visually or instrumentally observed.

According to further features in the described preferred embodiments, the formulation is in the form of a cream, an emulsion, or an ointment.

According to still further features in the described preferred embodiments, the total silver content of the formulation, or total silver content of the at least one silver-containing compound, is within a range of 0.0005% to 20%, 0.0005% to 12%, 0.0005% to 7%, 0.0005% to 3.5%, 0.0005% to 3%, 0.0005% to 2.5%, 0.001% to 3.5%, 0.005% to 3.5%, 0.01% to 3.5%, 0.03% to 3.5%, 0.05% to 3.5%, 0.10% to 3.5%, 0.30% to 3.5%, 0.5% to 3.5%, 0.7% to 3.5%, or 0.9% to 3.5%, by weight.

According to still further features in the described preferred embodiments, the aliphatic carboxylate content is at least 0.1%, on an $Ag_4O_4$ weight basis, the formulation being white or at least off-white.

According to still further features in the described preferred embodiments, the aliphatic carboxylate content is at least 0.1%, on an $Ag_4O_4$ weight basis, the formulation is white or at least off-white.

According to still further features in the described preferred embodiments, the formulation typically has a standard whiteness value of at least 3.4, at least 3.5, at least 3.6, at least 3.7, at least 3.8, or at least 3.9 reflective units (RU), at least within a range of 0.1% to 1.7%, on an $Ag_4O_4$ weight basis.

According to still further features in the described preferred embodiments, the total silver content of the at least one silver-containing compound is within a range of 0.09% to 1.7%, on an $Ag_4O_4$ weight basis, and the formulation has a standard whiteness value of at least 4.0, at least 4.1, at least 4.2, or at least 4.3 reflective units (RU).

According to still further features in the described preferred embodiments, the total silver content of the at least one silver-containing compound is within a range of 0.8% to 3.4%, by weight, and the formulation has a standard whiteness value of at least 3.5, at least 3.6, at least 3.7, at least 3.8, or at least 3.9 reflective units (RU).

According to still further features in the described preferred embodiments, the silver carboxylate and the carrier base are selected such that after standard ultraviolet light (UV) treatment, in which the formulation is subjected to constant exposure to UV for 12 hours at 240 nm, the standard whiteness value of the formulation remains within 0.6 RU, within 0.5 RU, within 0.4 RU, within 0.3 RU, or within 0.2 RU, of the initial whiteness value of the formulation prior to the treatment.

According to still further features in the described preferred embodiments, the silver carboxylate and the carrier base are selected such that standard ultraviolet light (UV) treatment, in which the formulation is subjected to constant exposure to UV for 12 hours at 240 nm, a post-UV whiteness value of the formulation remains at least 3.5 reflective units (RU), at least 3.6 RU, at least 3.7 RU, at least 3.8 RU, at least 3.9 RU, at least 4.0 RU, or at least 4.1 RU.

According to still further features in the described preferred embodiments, the formulation contains the silver carboxylate in a range of 0.30% to 3.5%, 0.4% to 3.5%, 0.5% to 3.5%, 0.6% to 3.5%, 0.7% to 3.5%, 0.30% to 3%, 0.4% to 3%, 0.5% to 3%, or 0.6% to 3%, by weight.

According to still further features in the described preferred embodiments, the average valence is at least 1.2, at least 1.3, at least 1.4, at least 1.5, at least 1.6, at least 1.7, at least 1.8, at least 1.9, or about 2.0.

According to still further features in the described preferred embodiments, the formulation contains less than 5%, less than 4%, less than 3%, less than 2.5%, less than 2.0%, less than 1.5%, less than 1.2%, less than 1%, less than 0.8%, less than 0.6%, or less than 0.4% of zinc oxide.

According to still further features in the described preferred embodiments, the formulation contains less than 5%, less than 4%, less than 3%, less than 2.5%, less than 2.0%, less than 1.5%, less than 1.2%, less than 1%, less than 0.8%, less than 0.6%, or less than 0.4% of a whitening agent such as an inorganic whitening agent.

According to still further features in the described preferred embodiments, the weight ratio of whitening agent to the at least one silver-containing compound is less than 7:1, less than 5:1, less than 3:1, less than 2:1, less than 1.5:1, less than 1.2:1, less than 1:1, less than 0.8:1, less than 0.6:1, less than 0.4:1, less than 0.3:1, less than 0.2:1, less than 0.1:1, or less than 0.05:1.

According to still further features in the described preferred embodiments, the whitening agent includes, primarily includes, or consists essentially of a divalent salt or oxide, such a calcium salt or oxide, or a magnesium salt or oxide.

According to still further features in the described preferred embodiments, the formulation contains less than 10%, less than 9%, less than 8%, less than 6%, less than 4%, less than 2%, less than 1%, less than 0.5%, less than 0.2%, less than 0.1%, or less than 0.05%, in total, of silver-containing compounds selected from the group consisting of silver(II) fluoride ($AgF_2$), silver(II) picolinate ($C_{12}H_8AgN_2O_4$) or any other silver(II) containing compound having a nitrogen atom in the ring or aromatic ring, silver(I) oxide and silver(II) oxide.

According to still further features in the described preferred embodiments, the at least one silver carboxylate includes a divalent or at least divalent silver carboxylate having a carbon number or average carbon number less than 40, less than 38, less than 36, less than 34, less than 33, less than 32, less than 31, less than 30 less than 29, less than 28, less than 27, less than 25, less than 23, less than 22, or less than 21.

According to still further features in the described preferred embodiments, the at least one silver carboxylate includes a divalent or at least divalent silver carboxylate having a carbon number or average carbon number greater than 9, greater than 10, or greater than 11.

According to still further features in the described preferred embodiments, the carbon number or average carbon number is less than 40 and greater than 11, less than 40 and greater than 13, less than 40 and greater than 14, less than 38 and greater than 11, less than 36 and greater than 11, less than 34 and greater than 11, less than 32 and greater than 11, less than 31 and greater than 11, less than 30 and greater than 11, less than 29 and greater than 11, less than 28 and greater than 11, or less than 27 and greater than 11.

According to still further features in the described preferred embodiments, the formulation contains at least one carboxylic acid, optionally including a corresponding carboxylic acid of the silver carboxylate having the nominal valence of at least 2, a molar ratio of the corresponding carboxylic acid to the silver carboxylate optionally being at least 0.01, at least 0.025, at least 0.05, at least 0.1, at least 0.2, at least 0.5, at least 1.0, at least 1.5, at least 2, or at least 3.

According to still further features in the described preferred embodiments, the hydrocarbon structure of the carboxylate is selected from at least one of the group consisting of fully saturated, monounsaturated, and polyunsaturated structures.

According to still further features, the backbone structure of the carboxylate includes at least one structure selected from the group consisting of a straight hydrocarbon chain and a branched hydrocarbon chain.

According to still further features, the backbone structure of the carboxylate includes at least one structure selected from the group consisting of a ring structure and an aromatic structure.

According to still further features, the carboxylate includes a silver carboxylate of a keto-carboxylic acid.

According to still further features, the formulation has, at 25° C., a viscosity of at least 25 cP, at least 100 cP, at least 250 cP, at least 500 cP, at least 1,000 cP, at least 5,000 cP, at least 20,000 cP, at least 50,000 cP, at least 150,000 cP, at least 500,000 cP, at least 1,000,000 cP, at least 3,000,000 cP, or at least 10,000,000 cP.

According to still further features, the formulation has a particular total silver content, and the concentration of elemental silver within the formulation is at most 50%, at most 30%, at most 15%, at most 5%, at most 3%, or at most 1% of the particular total silver content.

According to still further features, the carrier base including or predominantly including an oleaginous material that may include or predominantly include a material selected from the group consisting of beeswax, petrolatum, a liquid wax ester, an oil, and a polyethylene wax.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are used to designate like elements.

In the drawings:

FIG. 8 is a bar graph of formulation whiteness for formulations containing: (1): $Ag_4O_4$ (0.7%); (2): $Ag_2O$ (0.7%); and (4): Ag(II) picolinate (0.7%), each in a base containing beeswax (19.8%) and jojoba oil (79.5%), vs. an inventive formulation containing 0.7% silver distearate in a substantially identical base;

FIG. 9 is a bar graph of formulation whiteness for prior-art silver(II) oxide formulations containing: (1): $Ag_4O_4$ (0.1%); (2): $Ag_4O_4$ (0.7%); (3): $Ag_4O_4$ (1.5%); and (4): $Ag_4O_4$ (3%), before and after being subjected to UV exposure o;

FIG. 10 is a bar graph of formulation whiteness for prior-art silver(I) oxide formulations containing: (1): $Ag_2O$ (0.1%); (2): $Ag_2O$ (0.7%); (3): $Ag_2O$ (1.5%); and (4): $Ag_2O$ (3%), before and after being subjected to UV exposure;

DETAILED DESCRIPTION

Figure 1:
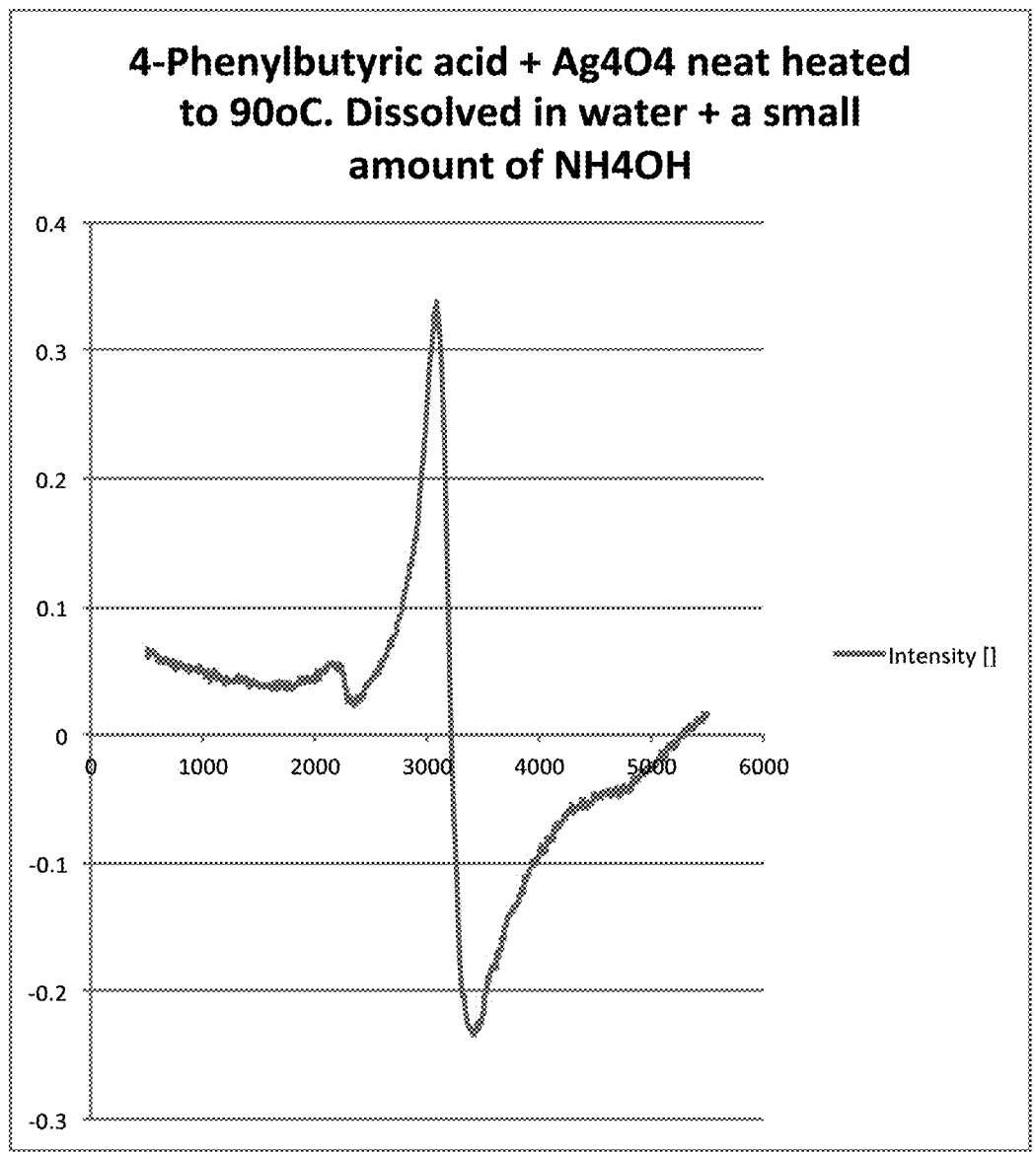
FIG. 1 provides an Electron Spin Resonance (ESR) spectrum for the reaction product of Example 4.

The principles of the silver(II) carboxylate formulations, methods of producing these formulations, and methods of use thereof, in accordance with the present invention, may be better understood with reference to the figures and the accompanying description.

Before explaining at least one embodiment of the invention in detail, it is to be understood that the invention is not limited in its application to the details set forth in the following description. The invention may be capable of other embodiments or of being practiced or carried out in various ways. Also, it is to be understood that the phraseology and terminology employed herein is for the purpose of description and should not be regarded as limiting.

$Ag_4O_4$ (tetrasilver tetroxide) may be particularly reactive with respect to other components in topical formulations, thereby compromising the stability of the formulation. The formulation may then acquire, disadvantageously, a dark brown or black color.

The inventors have discovered a method of preparing silver(II) carboxylate formulations having anti-microbial properties. Many of such formulations may advantageously have a light (e.g., light yellow, tan, or off-white) or white appearance.

Strikingly, and in sharp contrast to formulations containing silver(II) oxide and silver(I) oxide, the formulations of the present invention may exhibit no darkening, or at most a slight darkening, with increasing concentration of the silver-containing anti-microbial agent.

The silver(II) carboxylates in the inventive formulations may typically have a nominal valence of 2, or at least 2. The concentration of these silver(II) carboxylates within the formulations may be at least 20 ppm, and up to 15% or up to 20% by weight, or more. In some embodiments, the concentration of these silver(II) carboxylates is at least 30 ppm, at least 100 ppm, at least 0.05%, at least 0.10%, at least 0.3%, at least 0.5%, at least 0.7%, at least 1%, at least 2%, at least 3%, at least 5%, at least 7%, at least 10%, at least 15%, or at least 20%. It must be emphasized that concentrations as low as 20 ppm have been found to be highly efficacious, from an anti-microbial or antibiotic standpoint.

In some embodiments, the concentration of these silver carboxylates is at most 10%, at most 7%, at most 5%, at most 3.5%, at most 3%, or at most 2.5%. In some embodiments, the concentration of these silver carboxylates is within a range of 20 ppm to 50%, 20 ppm to 45%, 20 ppm to 40%, 20 ppm to 30%, 20 ppm to 20%, 20 ppm to 15%, 20 ppm to 10%, 20 ppm to 5%, 100 ppm to 3%, 0.05% to 3%, 0.1% to 3%, 0.2% to 3%, 0.3% to 3%, 0.5% to 3%, or 0.7 to 3%.

Formulations of the present invention have been found to possess antibiotic properties, i.e., they may attack and destroy at least one species or type of microorganism, while selectively exhibiting relative inertness with respect to human and mammalian cells. More typically, the antibiotic substance selectively attacks and destroys at least one species or type of microorganism that commonly populates the skin, surface wounds, bedsores and the like, while exhibiting relative inertness, with respect to skin cells of humans and mammals.

EXAMPLES

Reference is now made to the following examples, which together with the above description, illustrate the invention in a non-limiting fashion.

In these examples, the microbes used: *Escherichia coli* 35218 and *Staphylococcus aureus* 25923, and *Candida albicans* 10231 were obtained from American type culture collection (ATCC).

With regard to materials and equipment, silver(II) oxide was obtained from Ames Goldsmith Inc. (New Jersey, USA). The silver(II) oxide typically contains at least 90% $Ag_4O_4$, by weight, and may contain some AgO and $Ag_2O$.

$Ag_2O$ (Catalog no. S 1090), also known as silver (I) oxide, was obtained from Spectrum Chemicals (New Jersey, USA).

4-phenylbutyric acid and 2-ethyl-hexanoic acid were obtained from Sigma-Aldrich (items P21005 and 538701, respectively).

The SYTO® bacterial count kit and LIVE/DEAD® Funga Light™ Yeast Viability Kit were obtained from Invitrogen Inc. (Texas, USA). Bacterial culture broths and media were obtained from Remel Inc. (New York, USA).

The microbial shaking incubator (model 311DS, Labnet Inc.) and Attune Flow cytometer (Invitrogen Inc.) were used for bacterial culture and bacterial assay, respectively.

$^1H$ and $^{13}C$-NMR spectra were obtained on a Bruker DPX-300 spectrometer. Chemical shifts are expressed in ppm downfield from $Me_4Si$ (TMS), which is used as an internal standard. The values are given in the δ scale.

Low Resolution Mass Spectra (LRMS) were also obtained on a Q-TOF micro (Waters UK) spectrometer using ESI (Electron Spray Ionization).

Melting points were determined on a Fisher-Johns apparatus and were uncorrected.

Elemental silver analysis was carried out by Inductively-Coupled Plasma (ICP) Atomic Emission Spectroscopy (Ultima 2, Jobin Yvon Horiba).

Electron Spin Resonance (ESR) spectra were obtained on an X-band Elexsys E500 EPR spectrometer (Bruker, Karlsruhe, Germany).

Example 1

An exemplary general procedure for producing the formulations (e.g., ointments and silver carboxylate concentrates) according to the present invention is as follows:

The silver(II) oxide powder is weighed in a weighing dish. The carboxylic acid containing material, typically solid at room temperature, is weighed in the reaction vessel, and heated, typically to a temperature within the range of 88-93° C., to obtain a liquid medium. The black silver(II) oxide powder is introduced to the hot liquid, and the reaction mixture is vigorously stirred. Stirring is continued while maintaining the temperature at 88-93° C. for the remainder of this stage. Typically, the solution will gradually lighten as the reaction mixture is maintained at 88-93° C. A general color progression may be observed: the color of the reaction mixture may turn from black (after adding the silver(II) oxide) to olive green to dark yellow. In many cases, the color of the reaction mixture may continue to develop into a light yellow, and may further develop to off-white and finally to white.

The reaction time may be about 1.5 to 48 hours, depending on the nature of the particular carboxylate, the molar ratio of the silver(II) oxide to the carboxylic acid functional group, mixing conditions (including viscosity), and temperature. Optionally, the reaction may be deliberately curtailed in order to ensure a presence of $Ag_4O_4$ within the formulation.

For particularly viscous carboxylic acid containing materials, the viscosity of the reaction mixture may be lowered by introducing a lower carboxylic acid (e.g., a C12 acid), by introducing a lower (low carbon number) silver carboxylate (e.g., a silver(II) C12 carboxylate), or by returning a portion of the product material from a previously-produced batch of the silver(II) carboxylate.

The product material from Example 1 may undergo further formulation. For example, the product material may be mixed with an oil and/or a liquid wax ester such as jojoba oil. Optionally, one or more silver(I) carboxylates may be blended into the formulation. Also, one or more essential oils such as palmarosa oil may be introduced. Stirring may be continued, typically for 0.5 to 2 hours, during cooling of the mixture to below about 40° C. The formulation may then be poured into storage containers.

Example 2

An exemplary general procedure for producing an emulsion-based silver(II) carboxylate compositions and formulations according to the present invention is as follows: a liquid such as water may be mixed or blended at high speed in a formulation vessel, preferably with a thickening agent such as bentonite or hectorite. Mixing may be continued as the silver(II) carboxylate, preferably heated, is introduced. Optionally, an essential oil such as palmarosa oil may be added.

In some cases, a liquid wax ester may be heated and mixed with the silver(II) carboxylate, prior to introduction of the carboxylate to the formulation vessel.

Higher concentrations of the thickening agent (e.g., 4-7% bentonite) may be associated with thicker creams; lower concentrations of the thickening agent (e.g., 1-2% bentonite) may be associated with creams having a relatively low viscosity.

Example 3

30 grams of beeswax and/or a carboxylic acid is melted on a hot plate, typically at a temperature of approximately 100° C. After melting of the beeswax and/or the fatty acid, 1 gram of AgO is added. Care should be taken to ensure that the mixture does not burn.

From the initial dark black color, the mixture typically lightens, ultimately turning light yellow, off-white, or white. 20 g of emulsifying wax is then melted at around 90° C., and subsequently added to the above-described reaction mixture, and stirred vigorously. The temperature may then be slowly lowered to about 75° C. Care should be taken not to lower the temperature too much as it may cause hardening of the wax.

Separately, 680 grams of water and 70 grams of Bentonite clay may be blended in a high shear blender. The mixture may then be blended at the high setting for about 60 minutes.

Subsequently, 240 grams of jojoba oil may be added to the above mixture, while continuing with the blending process operation. At this point, 50 grams of the Ag-beeswax/carboxylic acid-emulsifying mixture may be added to the emulsion, while intensive blending may be continued for 40 minutes. The end product may be an emulsion containing a silver(II) carboxylate.

Example 4

A mixture of $Ag_4O_4$ (0.3 grams, 24.22 mmol) and 4-phenylbutyric acid (an aromatic aliphatic carboxylic acid) (3.97 g, 2.42 mmol) was stirred at 90° C. overnight. The reaction mixture, initially black, eventually turned white. A sample of about 10 mg of the white solid obtained was mixed with water and a small amount of concentrated ammonia and an ESR spectrum of the solution was taken. The ESR spectrum obtained, provided in FIG. 1, indicates the presence of a free radical such as $Ag^{+2}$. Based on various testing procedures described hereinbelow, the reaction product is silver(II) di-4-phenylbutyrate.

Figure 2:
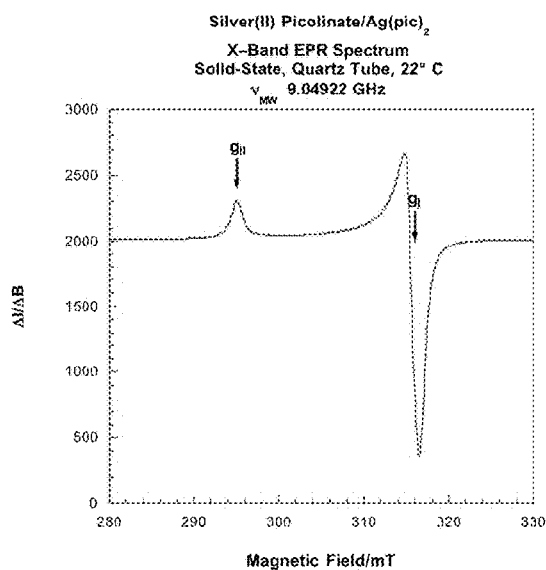
FIG. 2 provides a comparative ESR spectrum of Ag(II) picolinate.

An ESR spectrum of Ag(II) picolinate is provided in FIG. 2 for comparative purposes.

Example 5

A similar reaction to that described in Example 4 was carried out with $Ag_4O_4$ (0.2 grams, 1.61 mmol), while replacing the 4-phenylbutyric acid with 2-ethylhexanoic acid (1.86 grams, 10 mmol), a branched aliphatic carboxylic acid. The reaction mixture, initially black, gradually lightened, and ultimately turned white. $^{13}$C-NMR (300 MHz, DMSO-$D_6$) performed on the white solid yielded ppm δ in the 2-ethyl-hexanoic acid, the COOH carbon has a chemical shift of 177.34 ppm, whereas in the isolated silver salt the COO$^-$ carbon has a chemical shift of 179.4 ppm.

Example 6

Three (3.0) grams of $Ag_4O_4$ were introduced to 40 grams of palmitic acid. The reaction mixture was maintained within a range of 90° C. to 110° C. overnight, resulting in a white waxy material.

Figure 3:
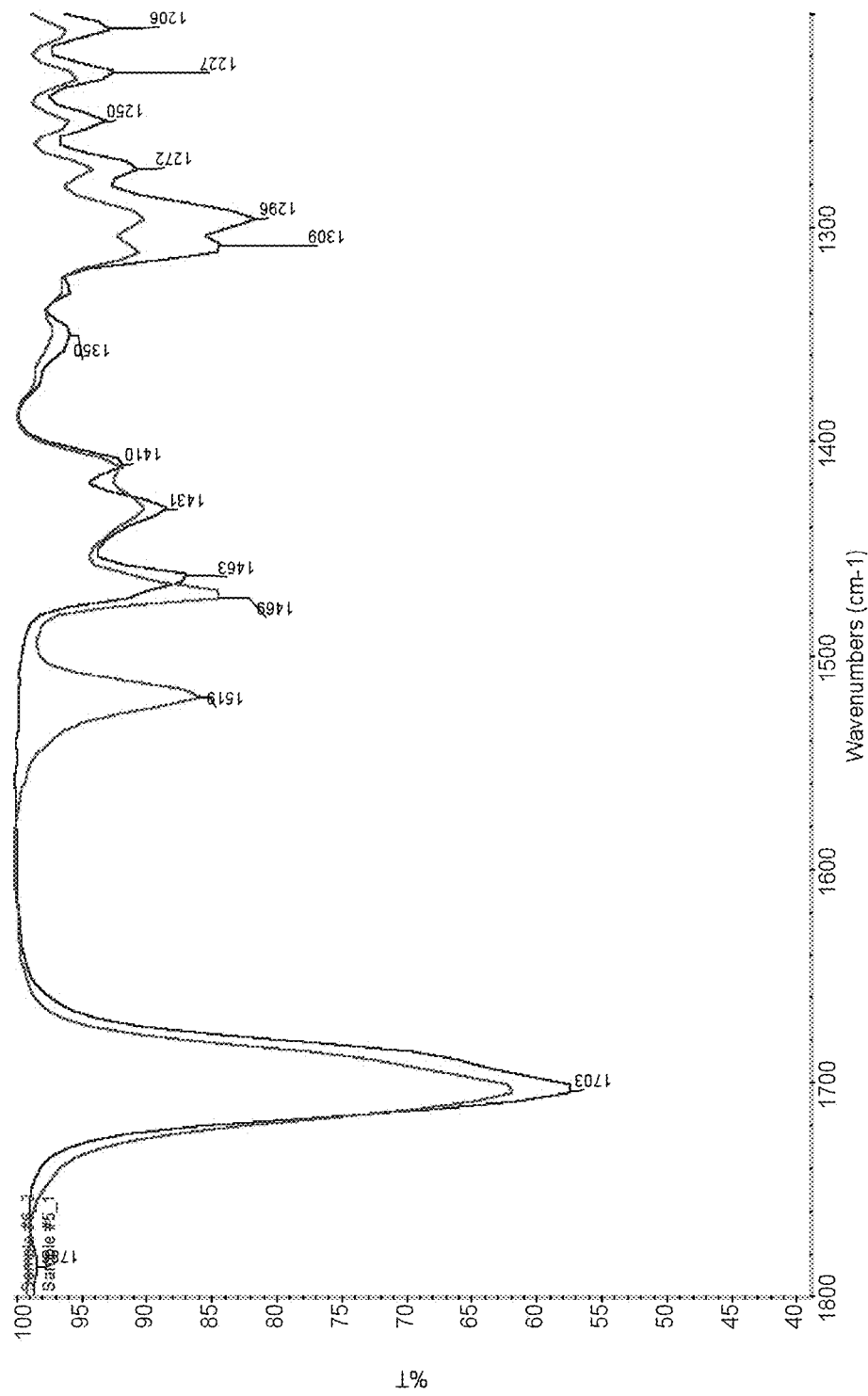
FIG. 3 provides an infra red (IR) spectroscopy plot of the reaction product of Example 6, vs. the spectrum of the palmitic acid feed material.

The resulting material was sent for infra red (IR) spectroscopy analysis and the results were compared to the spectrum of palmitic acid used in the synthesis. The IR plot obtained is provided in FIG. 3.

Peaks at wavenumbers 1519 and around 1420 (not resolved) may indicate the COO– asymmetric and symmetric stretching vibrations of a carboxylate. The 1519 peak exactly matches the peak for silver behenate reported by Liu et al. in "Thermal Decomposition Process of Silver Behenate", Thermochimica Acta 440 (2006) 1-6, Elsevier Press. These peaks are absent from the palmitic acid sample.

In addition, the C=O stretch at wavenumber 1703 and the C—O stretch at wavenumber 1296 are reduced from the fatty acid to the product, suggesting that the number of COOH groups is diminishing.

These pieces of evidence strongly suggest the formation of a silver carboxylate complex.

Examples 7-10

All of the reactions carried out in Examples 7-10 were performed using 1.5 grams of $Ag_4O_4$, containing about 0.012 moles of silver. These reactions were performed using n-Docosanol as a medium or vehicle, where the weight of the n-Docosanol and the fatty acid totaled 40 grams. The palmitic acid used contained 97.4% palmitic acid; the discrepancy from the pure material was accounted for in the molar calculations.

The results are summarized in Table 1. For molar ratios of 2:1 (carboxylic groups:$Ag_4O_4$, on an AgO basis) and above, a white solid was obtained, whereas for a molar ratio of 1.6:1, a light brown solid was obtained. It would appear than there was not enough carboxylic acid to react with the $Ag_4O_4$, consequently, the remaining $Ag_4O_4$, reacted with the solvent, or perhaps remained partially unreacted.

Additional support for the valence of the silver in the carboxylate is provided hereinbelow.

TABLE 1

| Example No. | Palmitic Acid | | $Ag_4O_4$ | | Molar Ratio (Ag:COO) | Final Color |
| --- | --- | --- | --- | --- | --- | --- |
| | g | moles COO | g | moles Ag | | |
| 7 | 20 | 0.076 | 1.5 | 0.012 | 6.3:1 | White |
| 8 | 10 | 0.038 | 1.5 | 0.012 | 3.2:1 | White |
| 9 | 6.4 | 0.024 | 1.5 | 0.012 | 2.0:1 | White |
| 10 | 5 | 0.019 | 1.5 | 0.012 | 1.6:1 | Light Brown |

Examples 11-14

All of the reactions carried out in Examples 11-14 were performed using 1.5 grams of $Ag_4O_4$, containing about 0.012 moles of silver. These reactions were performed using n-Docosanol as a medium or vehicle, where the weight of the n-Docosanol and the fatty acid totaled 40 grams. The behenic acid used contained 89.3% behenic acid; the discrepancy from the pure material was accounted for in the molar calculations.

The results are summarized in Table 2:

TABLE 2

| Example No. | Behenic Acid | | $Ag_4O_4$ | | Molar Ratio (Ag:COO) | Final Color |
| --- | --- | --- | --- | --- | --- | --- |
| | g | moles COO | g | moles Ag | | |
| 11 | 14.2 | 0.036 | 1.5 | 0.012 | 3.0:1 | White |
| 12 | 10.0 | ~0.024 | 1.5 | 0.012 | 2.0:1 | White (slightly off) |
| 13 | 9.7 | ~0.024 | 1.5 | 0.012 | 2.0:1 | Light Brown |
| 14 | 5 | 0.019 | 1.5 | 0.012 | 1.0:1 | Brown-Gray |

For molar ratios above 2:1, a white solid was obtained. In Example 13, slightly less behenic acid (0.3 grams less) was reacted with the $Ag_4O_4$, and the reaction mixture turned a light brown. As above, it would appear than there was not enough carboxylic acid to react with the $Ag_4O_4$, consequently, the excess $Ag_4O_4$, reacted with the solvent, or perhaps remained partially unreacted.

At a molar ratio of 1:1, significantly below 2:1, the reaction mixture turned brown-gray.

Examples 15-17

Each of the silver(II) palmitate of Example 7, silver(II) behenate of Example 11, and silver(II) 4-phenylbutyrate of Example 4 were incorporated into a carrier base containing beeswax and jojoba oil to produce the formulations of Examples 15-17 (1%/20% beeswax/79% jojoba oil). The formulation exhibited physical and chemical stability. Each of the silver(II) palmitate (Example 15), silver(II) behenate (Example 16), and silver(II) 4-phenylbutyrate formulations was examined over the course of 3-12 months to assess long term physical and chemical stability. No degradation of the formulations was observed: there was substantially no physical segregation of phases, and the formulations retained their light/white color over time.

Other samples of silver(II) carboxylates are the subject of an ongoing aging study. Various silver(II) carboxylate formulations have been subjected to ultraviolet (UV) light in an accelerated test procedure. The results, along with various comparative examples, are provided below in Examples 84-104.

Examples 18-29

A series of reactions between $Ag_4O_4$ and various aliphatic carboxylic acids was conducted generally according to the synthesis procedure provided in Example 1. In each synthesis, 80 grams of a particular carboxylic acid (ranging from C8 to C26) or 80 grams of beeswax were transferred into a reaction vessel.

All of these aliphatic carboxylic acids have melting points below 90° C. After melting the particular carboxylic acid or acids, as necessary, the temperature may be slowly increased to about 90-100° C. The reaction may be appreciably slower, or may fail to occur at lower temperatures, and above about 105° C., various side reactions may occur, or even predominate.

Subsequently, 3 grams of $Ag_4O_4$ were introduced, and the reaction mixture was stirred over the course of the reaction.

TABLE 3

| Example | Carboxylic Acid | Carbon No. | MW (g) | Conversion Time (h) | Color after conversion | Staining after UV exposure | Moles of Acid | Acid:Ag(II) molar ratio | % Weight of Ag(II) Carboxylate in Formulation |
|---|---|---|---|---|---|---|---|---|---|
| Example 18 | Caproic acid | C6 | 116.2 | NA | Black | NA | 0.688 | 28.4 | 9.9% |
| Example 19 | Caprylic acid | C8 | 144.2 | NA | Brown | NA | 0.555 | 22.9 | 11.6% |
| Example 20 | Capric acid | C10 | 172.3 | 4 h | Light Gray | Gray | 0.464 | 19.2 | 13.2% |
| Example 21 | Lauric acid | C12 | 200.3 | 3 h | White | Brown | 0.399 | 16.5 | 14.9% |
| Example 22 | Palmitic acid | C16 | 256.4 | 2 h | White | off-yellow | 0.312 | 12.9 | 18.1% |
| Example 23 | Beeswax acids | ~C18 | | 2-12 h | White/very white | off-white | | | |
| Example 24 | Stearic acid | C18 | 284.4 | 3-4 h | Very white | White | 0.281 | 11.6 | 19.8% |
| Example 25 | Nonadecyclic acid | C19 | 298.5 | 5-6 h | White | Off-white | 0.268 | 11.1 | 20.6% |
| Example 26 | Arachidic | C20 | 312.5 | 5-6 h | Off white | Off white | 0.256 | 10.6 | 21.4% |
| Example 27 | Behenic acid | C22 | 340.5 | 8 h | White | Brown | 0.235 | 9.7 | 23.1% |
| Example 28 | Lignoceric acid | C24 | 368.6 | 17 h | Yellow | Gray | 0.217 | 9.0 | 24.7% |
| Example 29 | Cerotic acid | C26 | 396.7 | 29 h | Dark yellow | Gray | 0.202 | 8.3 | 26.4% |

A general color progression was observed: the color of the reaction mixture typically turned from black (after adding the black silver(II) oxide powder) to olive green to dark yellow. In many cases, the color of the reaction mixture continued to develop, first into a light yellow, and with additional reaction time, to off-white and finally to white.

The reactions generally appeared to go to completion within about 3-30 hours, depending on the particular fatty acid.

About 320 grams of jojoba oil were heated to about 88° C. and were introduced to the reaction mixture after the reaction appeared complete. The mixture was then homogenized for about 30 seconds, gradually cooled to about 40° C., and transferred into storage containers.

The results of the reactions are summarized in Table 3 below.

Example 30

1. The bacterial cells were initially seeded in a culture flask containing tryptic soy agar, as per ATCC guidelines, in a 311DS incubator.
2. The cells take approximately 30 hours to reach 90% confluence. The cells were then individually seeded in test tubes containing 10 ml broth, and care was taken to maintain an identical cell count in each tube.
3. For each experimental time point, a control tube was seeded as well.
4. Sterile paper discs were handled in a biological hood and 1% of the test formulation was carefully smeared therein.
5. The disc was then dropped into the test tube with the bacterial broth and placed into the shaking incubator. At the same time, an "empty" disk was dropped into the control bacterial broth.
6. The process was repeated several times, using various formulations and run lengths.

Example 31

1. After the bacteria were allowed to be treated with a particular formulation for the designated time point (20-180 min), the tubes, along with a corresponding control, were removed from the incubator. Using sterile tweezers, the disc was removed and discarded and the bacteria were centrifuged at 5000 g for 30 seconds.
2. The bacterial pellet was re-suspended in 2 mL of fresh tryptic soy broth.
3. At this point, 2 μL of the SYTO® bacterial stain (component A) was added to the cells and incubated for 5 min
4. After the incubation, 10 μL of component B were added, and incubation was continued for another 5 minutes. The samples were then analyzed using a flow cytometer. The flow cytometer provides the results as a percentage of the control, and using that as a scale, the number of cells may be mathematically determined.
5. The bacterial count is ascertained based on the stainability with the SYTO® stain. A new kit was used every 2 weeks, as the components start degrading after about 15 days.

Using the above-mentioned technique, samples were analyzed for cell viability, and the results were documented, as provided hereinbelow.

Examples 32-41

Anti-Bacterial Performance of Aliphatic Silver(II) Carboxylates—*S Aureus*

Figure 4:
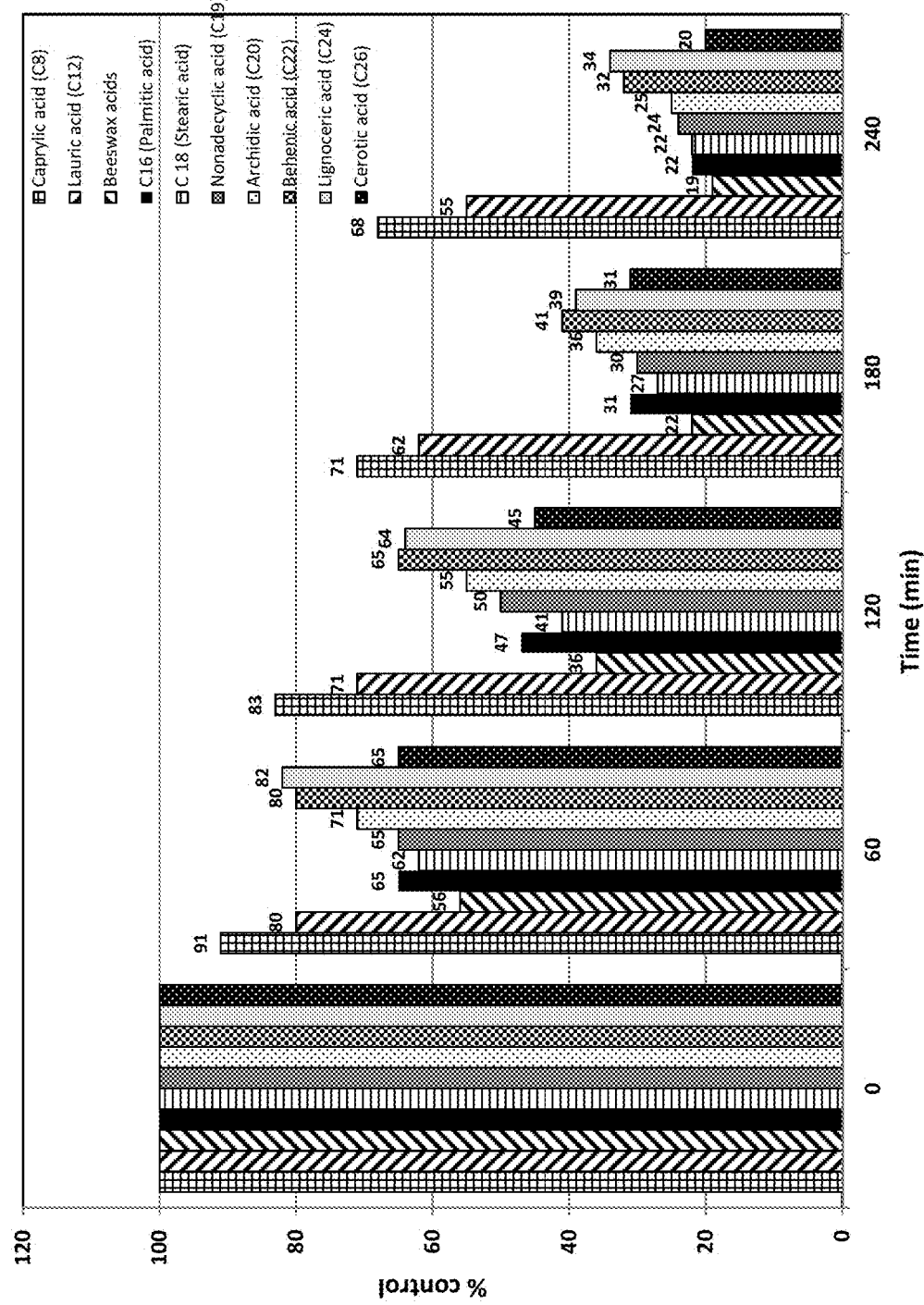
FIG. 4 is a bar graph showing the anti-bacterial performance, over time, of aliphatic silver(II) carboxylates of Examples 18-29, using *Staphylococcus aureus* 25923.

Using the above-provided techniques, the anti-bacterial performance of most of the aliphatic silver(II) carboxylates of Examples 18-29 was evaluated, using *Staphylococcus aureus* 25923. The results over time are shown in a bar graph in FIG. 4.

Over the course of 4 hours of measurements, all 10 of the silver(II)-containing formulations exhibited anti-bacterial activity. Of the 10 formulations, those having a carbon number above C12 appeared to be particularly efficacious, such that after 4 hours, the microbial count was reduced to about ⅕ to ⅓ of the control value.

Examples 42-51

Figure 5:
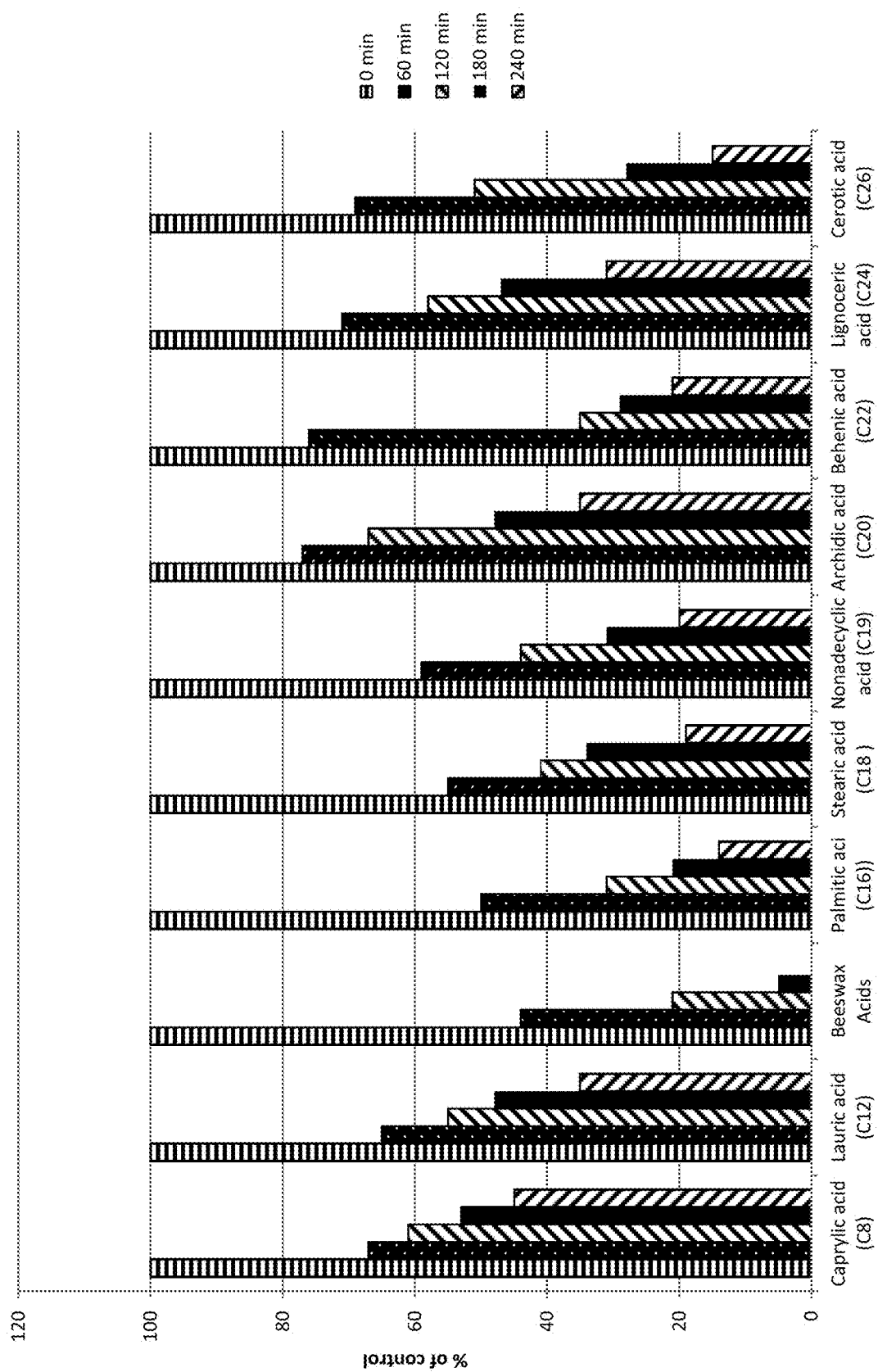
FIG. 5 is a bar graph showing the anti-bacterial performance, over time, of aliphatic silver(II) carboxylates of Examples 18-29, using *Escherichia coli* 35218.

Using the above-provided techniques, the anti-bacterial performance of most of the aliphatic silver(II) carboxylates of Examples 18-29 was evaluated, using *Escherichia coli* 35218. The results over time are shown in a bar graph in FIG. 5.

Over the course of 4 hours of measurements, all 10 of the silver(II)-containing formulations exhibited anti-bacterial activity. Of the 10 formulations, those having a carbon number above C12 appeared to be particularly efficacious, such that after 4 hours, the microbial count was reduced to about 0 to ⅓ of the control value.

Example 52

1. After treating the fungus sample with a particular formulation for the designated time point (20-180 min), the tubes, along with a corresponding control, were removed from the incubator. Using sterile tweezers, the disc was removed and discarded and the fungus sample was centrifuged at 1000 g for 60 seconds.
2. The fungal pellet was re-suspended in 2 ml of fresh saboraud liquid media.
3. At this point, 10 µl of the LIVE/DEAD® Funga Light™ Yeast Viability Kit were added to the cells and incubated for 5 minutes.
4. The samples were then analyzed using a flow cytometer. The flow cytometer provides the results as a percentage of the control, and using that as a scale, the number of cells may be mathematically determined.
5. The fungal count is ascertained based on the stainability with the LIVE/DEAD® Funga Light™ Yeast Viability Kit. A new kit was used every 2 weeks, as the components start degrading after about 15 days.

Examples 53-62

Figure 6:
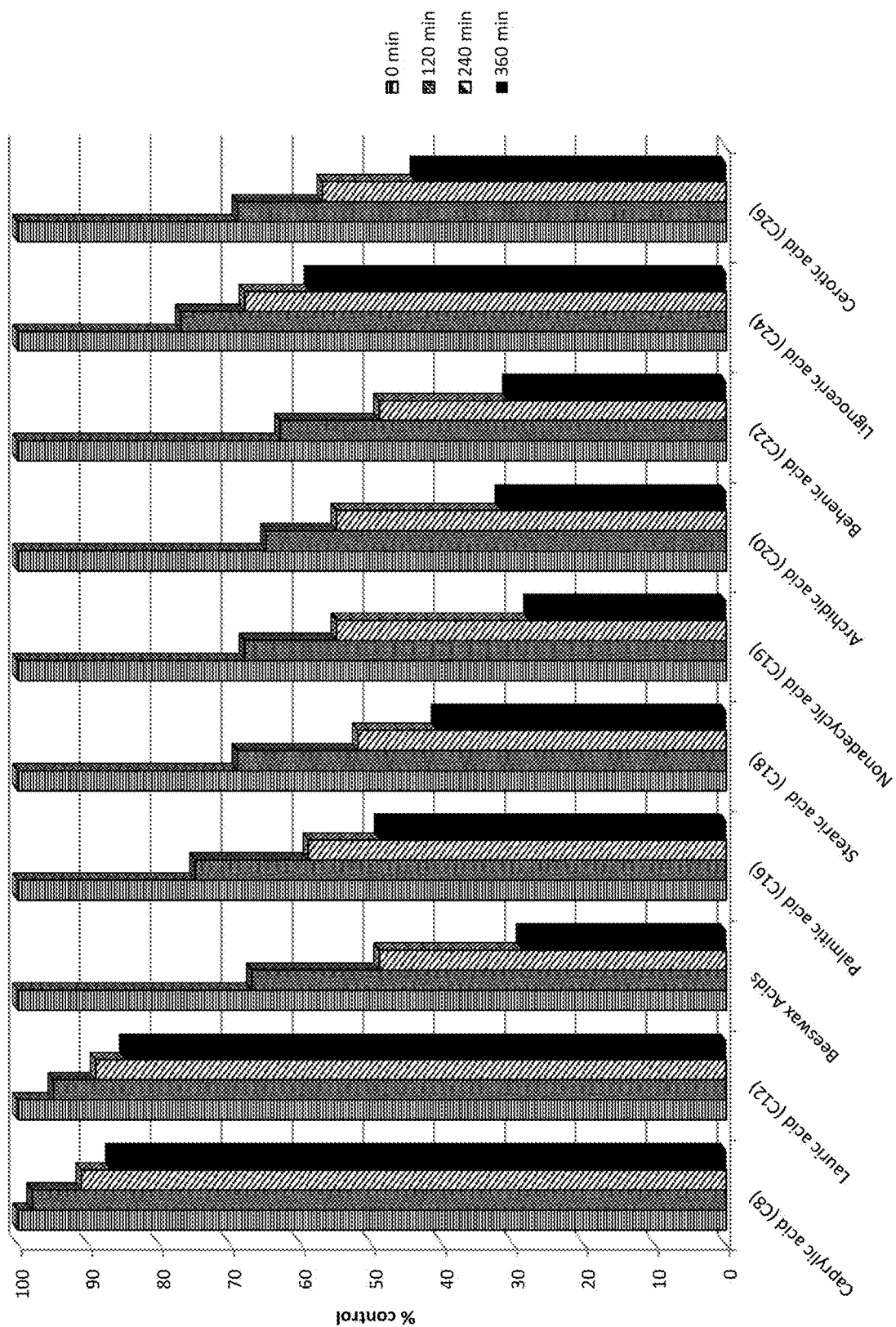
FIG. 6 is a bar graph showing the anti-fungal performance, over time, of aliphatic silver(II) carboxylates of Examples 18-29, using *Candida albicans* 10231.

Using the above-provided techniques, the anti-fungal performance of most of the aliphatic silver(II) carboxylates of Examples 18-29 was evaluated, using *Candida albicans* 10231. The results over time are shown in a bar graph in FIG. 6.

Over the course of 4 hours of measurements, all 10 of the silver(II)-containing formulations exhibited anti-fungal activity. Of the 10 formulations, those having a carbon number above C12 appeared to be particularly efficacious, such that after 6 hours, the microbial count was generally reduced by more than ½, and more typically, by about 60-75% relative to the control value.

Example 63

The synthesis procedure was conducted generally according to the procedure provided in Example 1. 30 grams of palmitic acid were heated in a reaction vessel to about 98° C.

Subsequently, 3 grams of $Ag_4O_4$ were introduced, and the reaction mixture was stirred over the course of about 48 hours. The color of the reaction mixture, initially black from the black silver(II) oxide powder, eventually turned white.

The concentrated silver(II) palmitate (also known as silver(II) dipalmitate) produced had a calculated concentration of about 46%, the remainder consisting primarily of excess palmitic acid.

Example 64

The emulsion was prepared generally according to the procedure provided in Example 3. About 680 grams of water were introduced to a high shear blender, and 70 grams of Bentonite clay were added thereto. The mixture was blended at a high setting for 60 minutes.

In a beaker, 240 grams of jojoba oil were heated to about 93° C., and 10 grams of the concentrated silver(II) palmitate formulation of Example 62 were introduced. The mixture was then homogenized for 1 minute.

This mixture was then added to the water-Bentonite base, and the new mixture was stirred at high speed for about 40 minutes.

The obtained formulation was an emulsion containing approximately 0.5% silver(II) palmitate.

Example 65

The emulsion was prepared according to the procedure provided in Example 64, but only 2 grams of the concentrated silver(II) palmitate formulation of Example 63 were introduced.

The obtained formulation was an emulsion containing approximately 0.1% silver(II) palmitate.

Examples 66-68

1.4 grams $Ag_4O_4$ were introduced to heated beeswax, mixing to produce the silver(II) carboxylate, using the process described in Example 1.

50 grams of the melted silver(II) carboxylate in beeswax were then added to 50 grams of previously melted petrolatum (Example 66), AC-629 (Example 67) and coconut oil (Example 68), in separate vessels, heated to about 80° C. Each mixture was then homogenized and cooled.

All three of the ointments were found to act as powerful anti-microbial agents.

Examples 69-71

$Ag_4O_4$ was introduced to heated beeswax, as described in the previous examples.

10 grams of the melted silver(II) carboxylate in beeswax were then added to 50 grams of previously melted petrolatum (Example 69), AC-629 (Example 70) and coconut oil (Example 71), in separate vessels, heated to about 80° C. Each mixture was then homogenized and cooled.

All three of the ointments were found to act as powerful anti-microbial agents.

Example 72

An ointment based on silver(I) carboxylate and jojoba oil was prepared generally according to Example 1, but using a commercially-available silver(I) palmitate.

The ointment, containing about 2.2% silver carboxylate, by weight, was found to exhibit anti-microbial activity.

Example 73

An ointment based on silver(I) carboxylate was prepared generally according to Example 66, but using a commercially-available silver(I) stearate, instead of reacting the silver(II) oxide with beeswax.

The ointment, containing about 1.3% silver carboxylate, by weight, was found to exhibit anti-microbial activity.

Example 74

Silver(II) palmitate from Example 22 and silver(I) palmitate from Example 72 were heated separately and mixed in a 1:6 ratio to produce a mixed silver(I)-silver(II) Carboxylate Formulation. The resulting formulation was found to exhibit anti-microbial activity.

Example 75

Silver(II) laurate from Example 21 and silver(I) palmitate from Example 72 were heated separately and mixed in a 1:9 ratio. The resulting formulation was found to exhibit anti-microbial activity.

Example 76

Determination of the organic acid bound to the silver in a cream or ointment, and determination of the oxidation state of the silver ion in the silver carboxylate found therein, may be performed as follows:

A sample of the cream was mixed with toluene to remove lipophilic materials, leaving organic salts in the solid or semi-solid phase. The mixture was centrifuged and the supernatant was decanted. The residue was washed with ether to remove remaining traces of toluene, and the residue was dried.

The residue was then mixed with an excess of trifluoroacetic acid, to convert any silver carboxylates to silver trifluoroacetate, and freeing the carboxylates as the corresponding free carboxylic acids. The obtained mixture was evaporated. The residue was mixed with ether and centrifuged, and the supernatant was separated and evaporated.

The residue, obtained after evaporation of the ether, was analyzed by $^1$H-NMR (300 MHz, CDCl$_3$). The residue produced a spectrum having the following characteristics: ppm δ 0.90 (t, 3H), 1.25 (bs, 28H), 1.61 (q, 2H), 2.24 (t, 2H), which indicates that the compound present was stearic acid. However, the integration of the peak at 1.25 ppm indicates the presence were a small amount of additional hydrogens, which may be attributable of a small amount (less than 10% of the acids present) of behenic acid.

A second sample of the residue (207 mg) obtained after mixing the cream with toluene, was dissolved in a small amount of concentrated nitric acid. The nitric acid solution was washed with ether, the ether was decanted, and the aqueous phase was diluted with water.

An elemental silver analysis by ICP revealed that the amount of the silver obtained (33.6 mg/L) corresponded, within a ~97% accuracy, to the calculated concentration of silver in a mixture of silver distearate (90%) and silver dibehenate (10%).

The 207 mg of residue, when composed of 90/10 distearate/dibehenate, gives a calculated value of silver of 32.5 mg/L. This theoretical value of 32.5 mg/L is within 3% of the found value of 33.6 mg/L, indicating that the oxidation state of the silver ion was Ag$^{+2}$. Had the salt obtained been that of Ag$^{+1}$ ion, the calculated amount of silver in 207 mg of residue would have been 49 mg/L.

Figure 7:
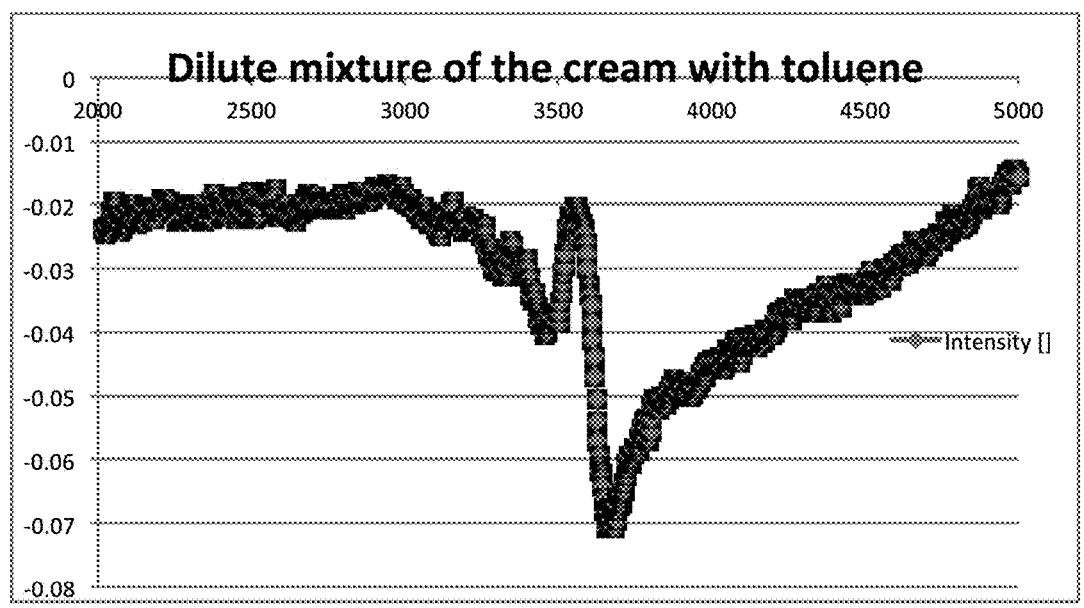
FIG. 7 provides an ESR spectrum for a mixture of silver distearate (90%) and silver dibehenate (10%)

Moreover, the ESR spectrum obtained, provided in FIG. 7, would appear to confirm the presence of Ag$^{+2}$.

Example 77

Formulation reflectance, lightness, or whiteness was evaluated as follows: approximately 1 gram of a particular sample (typically an ointment or cream) was spread on a 5 cm by 5 cm area of white cotton cloth and distributed evenly, typically using a metal spatula.

A LabScan XE spectrophotometer instrument (Hunter-Lab, VA) was used to evaluate the reflectance of each sample. The working principle of the instrument pertains to the property of light reflection. The cloth sample is stored in a completely dark container. To measure the reflectance, the instrument exposes the sample to a controlled, repeatable pulse of light. The lightness of the sample is generally correlated with the reflectance: higher values correspond to lighter samples.

The spectrophotometer has a wavelength range of 375 nm to 750 nm and an optical resolution of 10 nm. The spectrophotometer measures reflected color using a 0°/45° geometry.

Example 78

Formulation reflectance was evaluated as a function of the exposure time to ultraviolet light, as follows: the LabScan XE spectrophotometer described in Example 74 was used. Each sample was continuously exposed to ultraviolet light produced by the illumination source. The continuous UV exposure is through a 254 nm, 6 W UV bulb distributed by Cole-Parmer®. The distance between the UV source and the specimen or formulation was 18 inches (~45.7 cm).

Sample preparation was substantially the same as that described in Example 74. After an initial measurement ("time 0"), additional measurements were made over the course of the exposure to ultraviolet light, typically after 12 or 24 hours.

Examples 79-83

FIG. 8 is a bar graph plotting formulation whiteness for formulations containing: (1): Ag$_4$O$_4$ (0.7%); (2): Ag$_2$O (0.7%); and (4): Ag(II) picolinate (0.7%), each in a base containing beeswax (19.8%) and jojoba oil (79.5%), vs. an inventive formulation containing 0.7% silver distearate in a substantially identical base.

Examples 84-87

FIG. 9 is a bar graph plotting formulation whiteness for prior-art formulations containing: (1): Ag$_4$O$_4$ (0.1%); (2): Ag$_4$O$_4$ (0.7%); (3): Ag$_4$O$_4$ (1.5%); and (4): Ag$_4$O$_4$ (3%), each in a base containing jojoba oil and beeswax in about a 4:1 weight ratio. After an initial measurement prior to UV exposure, an additional measurement was made after 12 hours of exposure to ultraviolet light (see Examples 77-78).

Examples 88-91

FIG. 10 is a bar graph plotting formulation whiteness for prior-art formulations containing: (1): Ag$_2$O (0.1%); (2): Ag$_2$O (0.7%); (3): Ag$_2$O (1.5%); and (4): Ag$_2$O (3%), each in a base containing jojoba oil and beeswax in about a 4:1 weight ratio. After an initial measurement prior to UV exposure, an additional measurement was made after 12 hours of exposure to ultraviolet light (see Examples 77-78).

Examples 92-95

Figure 11:
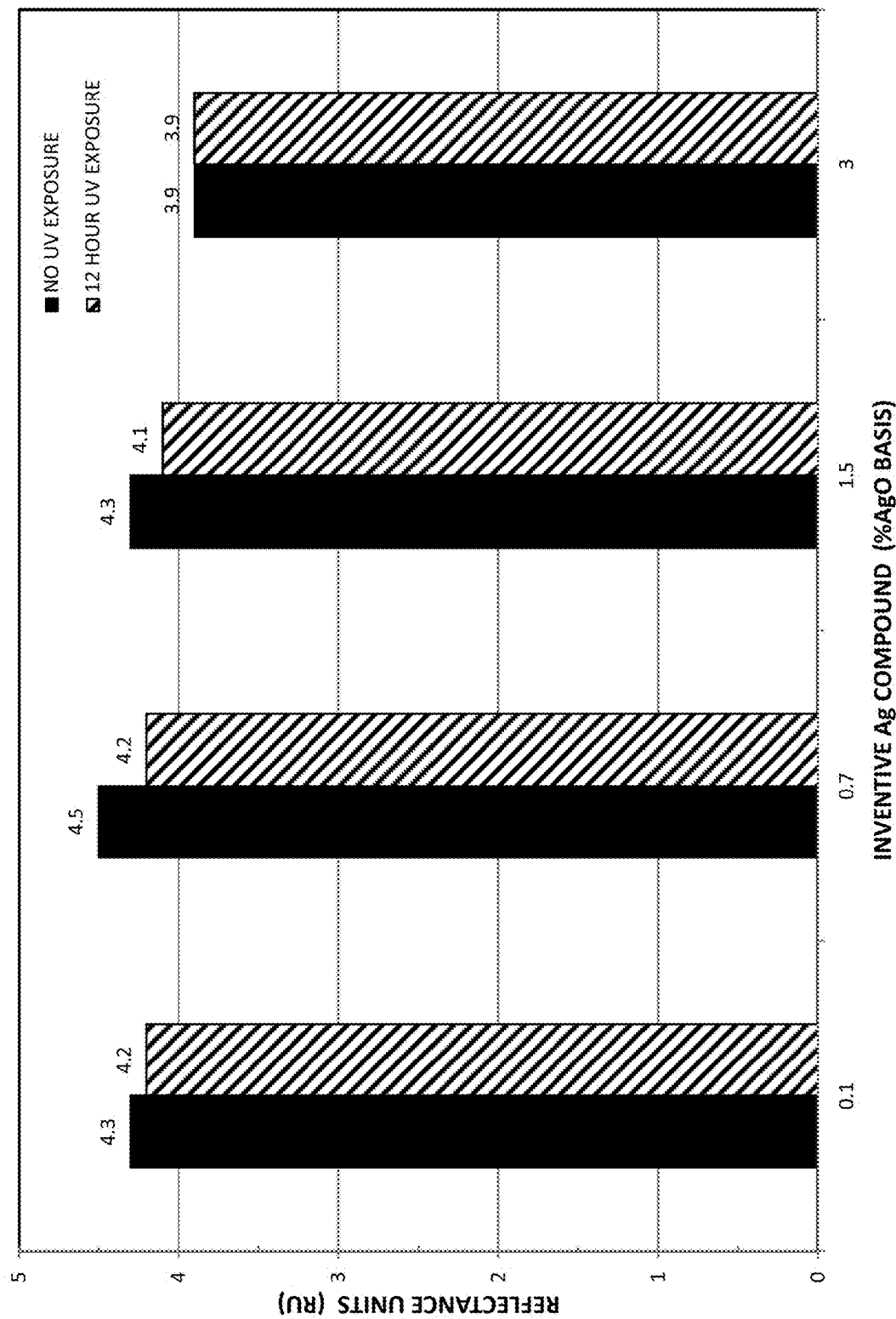
FIG. 11 is a bar graph of formulation whiteness for inventive formulations produced from $Ag_4O_4$ and beeswax, before and after being subjected to UV exposure.

FIG. 11 is a bar graph plotting formulation whiteness for formulations according to the present invention, the formulations containing: (1): Ag(II) carboxylate (0.1% on an Ag$_4$O$_4$ basis); (2): Ag(II) carboxylate (0.7% on an Ag$_4$O$_4$ basis); (3): Ag(II) carboxylate (1.5% on an Ag$_4$O$_4$ basis); and (4): Ag(II) carboxylate (3% on an Ag$_4$O$_4$ basis); each disposed in a base containing jojoba oil and beeswax in about a 4:1 weight ratio. The Ag(II) carboxylate was produced from $Ag_4O_4$ and beeswax. After an initial measurement prior to UV exposure, an additional measurement was made after 12 hours of exposure to ultraviolet light (see Examples 77-78).

Examples 96-98

Figure 12:
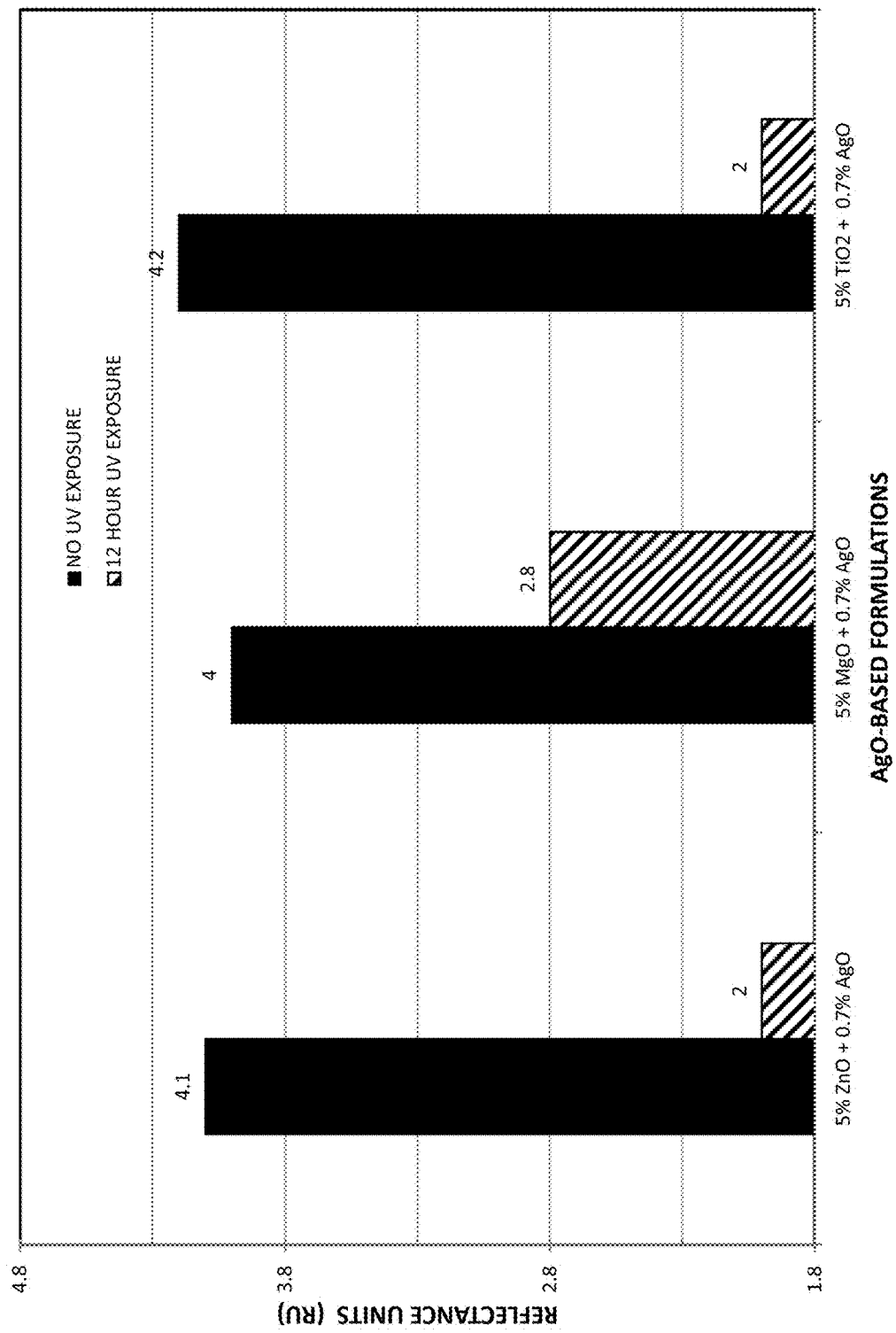
FIG. 12 is a bar graph of formulation whiteness for prior-art formulations containing $Ag_4O_4$ and various inorganic whiteners, before and after being subjected to UV exposure.

FIG. 12 is a bar graph plotting formulation whiteness for prior-art formulations containing: (1): 5% ZnO and 0.7% $Ag_4O_4$; (2): 5% MgO and 0.7% $Ag_4O_4$; and (3): 5% $TiO_2$ and 0.7% $Ag_4O_4$, each in a base containing jojoba oil and beeswax in about a 4:1 weight ratio. After an initial measurement prior to UV exposure, an additional measurement was made after 12 hours of exposure to ultraviolet light (see Examples 77-78).

Examples 99-101

Figure 13:
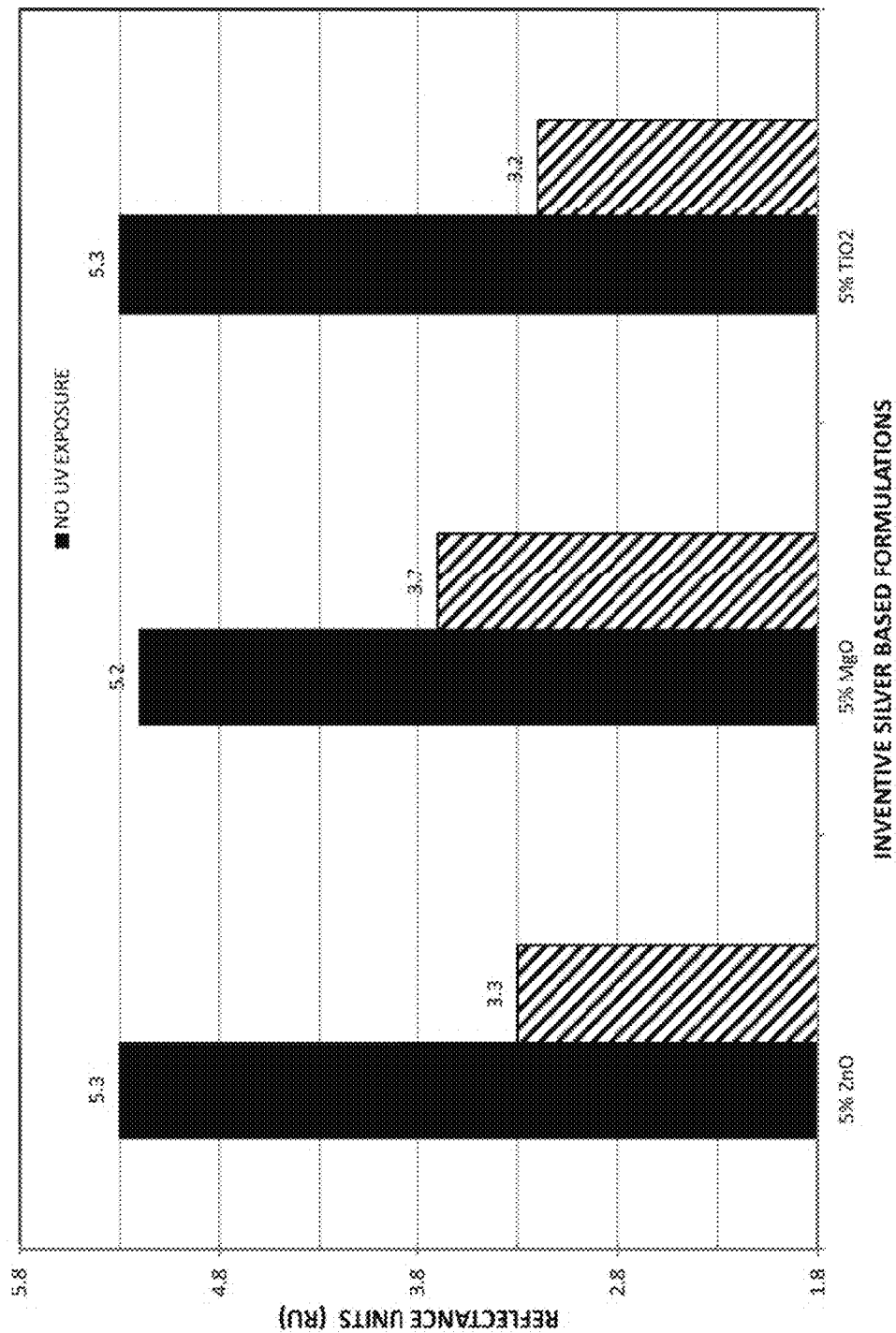
FIG. 13 is a bar graph of formulation whiteness for inventive formulations produced from $Ag_4O_4$ and beeswax, before and after being subjected to UV exposure, some of the formulations containing various inorganic whiteners.

FIG. 13 is a bar graph plotting formulation whiteness for formulations according to the present invention, the formulations containing: (1): Ag(II) carboxylate (0.7% on an $Ag_4O_4$ basis) and 5% ZnO; (2): Ag(II) carboxylate (0.7% on an $Ag_4O_4$ basis) and 5% MgO; and (3): Ag(II) carboxylate (0.7% on an $Ag_4O_4$ basis) and 5% $TiO_2$; each disposed in a base containing jojoba oil and beeswax in about a 4:1 weight ratio. The Ag(II) carboxylate was produced from $Ag_4O_4$ and beeswax. After an initial measurement prior to UV exposure, an additional measurement was made after 12 hours of exposure to ultraviolet light (see Examples 77-78).

Examples 102-104

Figure 14:
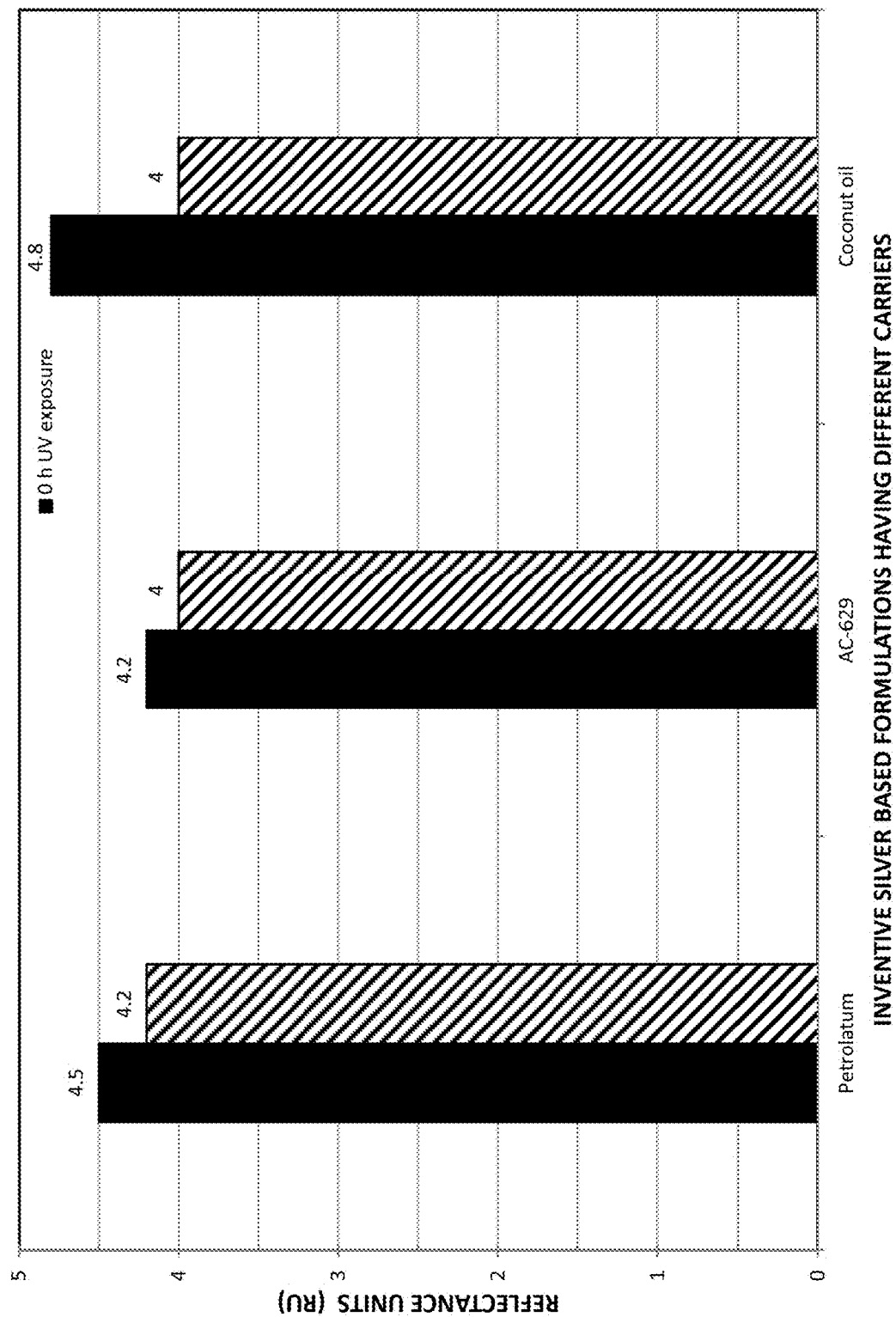
FIG. 14 is a bar graph of formulation whiteness for inventive formulations containing a silver(II) carboxylate in various bases, before and after being subjected to UV exposure.

FIG. 14 is a bar graph plotting formulation whiteness for formulations according to the present invention, the formulations containing: (1): Ag(II) carboxylate (0.7% on an $Ag_4O_4$ basis) in a petrolatum base; (2): Ag(II) carboxylate (0.7% on an $Ag_4O_4$ basis) in an AC-629 base; (3): Ag(II) carboxylate (0.7% on an $Ag_4O_4$ basis) in a coconut oil base. The Ag(II) carboxylate was produced from $Ag_4O_4$ and beeswax. After an initial measurement prior to UV exposure, an additional measurement was made after 12 hours of exposure to ultraviolet light (see Examples 77-78).

Examples 105-113

Ag(II) carboxylate formulations were prepared according to the procedure provided for Examples 21-29, but with 2.4 grams of silver(II) oxide (instead of 3 grams). After being stored in airtight plastic storage containers, the color and texture of the formulations were monitored in tri-monthly fashion. These formulations exhibited no phase separation or darkening/color change after three months, six months, 9 months or 1 year of storage at room temperature. To date, after 14 months of storage, the formulations look substantially identical to similar, newly produced Ag(II) carboxylate formulations. Moreover, the aged formulation continued to exhibit strong anti-microbial activity.

Example 114

Viral Assay Protocol

Seeding Healthy NRK 52E (Rat Kidney Epithelial Cells):
1. Make three substantially identical base solutions of cells, each solution having $1 \cdot 10^6$ cells per mL in Growth Media:
Solution 1: control solution;

Solution 2: introduce to the second base solution about 0.1% by weight of an inventive homeopathic, wart formulation containing 0.7% silver(II) carboxylate on an AgO basis, 0.2% liquid containing alcohol (67%), water (33%), and a trace of thuja occidentalis extract, all disposed within a base containing ~3.5:1 jojoba oil to beeswax; and
Solution 3: introduce to the third base solution about 0.1% by weight of an inventive wart stick containing 0.7% silver (II) carboxylate on an AgO basis and salicylic acid (12%) both disposed within a base containing ~5:1 jojoba oil to beeswax;
2. Vortex all three solutions;
3. Add 1.0 mL of growth media with cells to a 6 well plate; and
4. Incubate plates in a 37° C., 5% $CO_2$ incubator. After ~12-24 hours, the cells should be ~90-100% confluent.
Preparing Adenovirus for Infection:
1. Prepare 4 tubes, each tube containing 2 mL of PBS;
2. Add 20 μL of virus sample to the first tube;
3. Vortex thoroughly.
Infecting the Cells with the Virus:
1. Pipette off and discard 5 mL of media from each well. One mL of media should now remain in each monolayer;
2. Add 100 uL of the viral solution to each well; at this point there should be three 6 well plates: control, terrasil with homeopathic and terrasil with salicylic acid, each infected with adenovirus;
3. Incubate the infected monolayer/s for 24 hours at 37° C.
Agar Overlay:
1. Prepare a sterile solution of 4% agarose in distilled water by autoclaving at 121° C. for 20 minutes;
2. Cool down the agarose to 37° C.;
3. Gently overlay 3 mL of agarose into each well of the three samples, and allow to solidify for 15 minutes;
4. Move the plate(s) to a humidified incubator at 37° C. having 10% $CO_2$;
Deep purple plaques will be visible 48-72 hours after infection. Plaques are visible to the naked eye and can be counted by placing the well plates on top of a light source.

Examples 115-116

| Viral Assay -- Results | |
|---|---|
| Sample No. | Approximate No. of Plaques |
| Control | 67 |
| Example 114: | 21 |
| Example 115: | 13 |

Example 117

Reaction between $Ag_4O_4$ and linoleic acid (a polyunsaturated omega-6 fatty acid) was conducted generally according to the synthesis procedure provided in Example 1. Linoleic acid, a liquid at room temperature, was heated to ~93° C. in a reaction vessel.

Subsequently, 3.75 grams of $Ag_4O_4$ were introduced, and the reaction mixture was stirred over the course of the reaction. The color of the reaction mixture gradually turned from dark gray, after adding the black silver(II) oxide powder, to yellow to off-white. The white solids produced were separable from the liquor, and displayed anti-microbial efficacy.

Example 118

Reaction between $Ag_4O_4$ and oleic acid (a monounsaturated fatty acid) was conducted according to the synthesis procedure provided in Example 117, using the same quantities of $Ag_4O_4$ and fatty acid. The color of the reaction mixture gradually turned from dark gray, after adding the black silver(II) oxide powder, to yellow to off-white. The white solids produced were separable from the liquor, and displayed anti-microbial efficacy. The conversion of linoleic acid appeared to transpire more rapidly than the conversion of oleic acid.

The inventors believe that in the formulations of the present invention, ketone moieties may substitute hydrogen moieties along the length of the hydrocarbon chain (except within 1-2 positions from the acid moiety). Such structures may be largely impervious attack by the silver(II) oxide during the synthesis. Similarly, halogen moieties, most typically chlorine moieties, may generally substitute hydrogen moieties along the length of the hydrocarbon chain.

The methods provided herein were found to be particularly suitable for carboxylic acids, and more specifically, aliphatic carboxylic acids such as fatty acids, having a melting point below 105° C., and more typically, below 102° C., below 100° C., below 98° C., below 96° C., below 93° C., or below 90° C. Carboxylic acids having melting points well below these temperatures tended to convert to the ($Ag^{+2}$) carboxylate with yet greater facility.

The conversion of monounsaturated and polyunsaturated acids may occur with relative facility with respect to the corresponding saturated acid.

As used herein in the specification and in the claims section that follows, the term "antimicrobial", with respect to a chemical agent or formulation, refers to a substance that is destructive to microorganisms, or inhibits the growth thereof.

As used herein in the specification and in the claims section that follows, the term "antibiotic" refers to a substance that selectively attacks and destroys at least one species or type of microorganism, while exhibiting relative inertness with respect to human and/or mammalian cells. More typically, the antibiotic substance selectively attacks and destroys at least one species or type of microorganism that commonly populates the skin, surface wounds, bedsores and the like, while exhibiting relative inertness, with respect to skin cells of humans and/or mammals. The term "antibiotic" is specifically meant to exclude anti-microbial preservatives, both anti-fungal preservatives and anti-bacterial preservatives. Such anti-fungal preservatives include, but are not limited to, compounds such as benzoic and ascorbic acids and alkali salts thereof, and phenolic compounds such as methyl, ethyl, propyl and butyl p-hydroxybenzoate (parabens). Antibacterial preservatives include, but are not limited to, compounds such as quaternary ammonium salts, alcohols, phenols, mercurials and biguanidines. The term "antibiotic" is specifically meant to exclude anti-microbial preservatives such as table salt and the like, vinegar, sodium nitrate, sodium nitrite, and sulfites. The term "antibiotic" is specifically meant to include, without being limited to, silver oxides such as silver(I) oxide and silver(II) oxide, silver sulfadiazine, and any other topical antibiotics that are efficacious in the treatment of serious skin wounds such as bedsores, skin ulcers, and puncture wounds, or that are efficacious in the treatment of mundane skin wounds. The term "antibiotic" is specifically meant to include "classic" topical antibiotics such as Bacitracin, Neomycin, Erythromycin and Chloramphenicol. Additional topical antibiotic substances may be readily apparent to those of ordinary skill in the art.

As used herein in the specification and in the claims section that follows, the term "therapeutically effective amount", with respect to an antibiotic substance or formulation, refers to a quantity sufficient to produce a positive result in the treatment of at least one topical infection.

As used herein in the specification and in the claims section that follows, the term "therapeutically effective concentration", with respect to an antibiotic substance within a formulation or medical device, refers to a concentration of the antibiotic, within the formulation or medical device, sufficient to produce a positive result in the treatment of at least one topical infection.

As used herein in the specification and in the claims section that follows, the term "percent", or "%", refers to percent by weight, unless specifically indicated otherwise.

As used herein in the specification and in the claims section that follows, the term "$Ag_4O_4$ weight basis" refers to a weight basis obtained by multiplying the silver weight content of a material by a factor of (AgO/Ag), or about 1.148.

Similarly, the term "ratio", as used herein in the specification and in the claims section that follows, refers to a weight ratio, unless specifically indicated otherwise.

As used herein in the specification and in the claims section that follows, the term "silver (II) oxide" refers to a silver oxide whose unit structure contains silver and oxygen in a substantially 1:1 molar ratio. The term "silver (II) oxide" is specifically meant to include $Ag_4O_4$ (often represented as $Ag_2O_3.Ag_2O$) and AgO.

As used herein in the specification and in the claims section that follows, the term "nominal valence", with respect to silver in a silver carboxylate, refers to an average valence of the silver within the silver carboxylate compound (molecule, salt, complex, etc.). Thus, by way of example, silver in a silver(II) carboxylate represented as Ag(OOCR)$_3$.AgOOCR would have a nominal valence of 2.

As used herein in the specification and in the claims section that follows, the term "corresponding" with respect to a carboxylic acid, refers to the acid form of a silver carboxylate. Thus, palmitic acid is the corresponding carboxylic acid of a silver palmitate.

As used herein in the specification and in the claims section that follows, the term "silver containing compound" is specifically meant to exclude metallic silver) ($Ag^0$). The term "silver containing compound" is specifically meant to include dissociated silver species, and/or silver species forming a complex.

As used herein in the specification and in the claims section that follows, the term "silver (I) oxide" refers to a silver oxide whose unit structure contains silver and oxygen in a substantially 2:1 molar ratio. The term "silver (I) oxide" is specifically meant to include $Ag_2O$.

As used herein in the specification and in the claims section that follows, the term "standard whiteness value", and the like, is meant to refer to the procedure detailed in Example 77.

As used herein in the specification and in the claims section that follows, the term "standard ultraviolet light (UV) treatment", and the like, is meant to refer to the procedure detailed in Example 78.

As used herein in the specification and in the claims section that follows, the term "largely includes", "consists largely of" and the like, with respect to a component within a formulation, refers to a content of at least 30%, by weight;

the term "mainly includes", "consists mainly of," and the like, refers to a content of at least 50%, by weight; the term "predominantly includes", "consists predominantly of", and the like, refers to a content of at least 65%, by weight.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. An antimicrobial formulation comprising:
(a) at least one silver-containing compound, including an anti-microbial agent containing an aliphatic silver carboxylate, said silver of said aliphatic carboxylate having a nominal valence of 2, wherein an average valence of silver in said at least one silver-containing compound is within a range of 1.1 to 2; and
(b) a carrier base;
said at least one silver-containing compound being dispersed within said base,
the formulation having a form of a cream, an emulsion, or an ointment, a total silver content of the formulation being within a range of 0.0005% to 7%, wherein a hydrocarbon structure of said aliphatic silver carboxylate is selected from the the group consisting of fully saturated, monounsaturated, and polyunsaturated structures; and wherein said aliphatic silver carboxylate is a divalent silver carboxylate having a carbon number greater than 9, and less than 27.

2. The formulation of any claim 1, wherein a content of said aliphatic silver carboxylate is at least 0.1%, on an $Ag_4O_4$ weight basis, the formulation being white or at least off-white.

3. The formulation of claim 1, wherein at least one of said silver carboxylate and said carrier base is selected, such that after standard ultraviolet light (UV) treatment, in which the formulation is subjected to constant exposure to UV for 12 hours at 240 nm, a post-UV whiteness value of the formulation remains at least 3.5 reflective units (RU).

4. The formulation of claim 1, wherein an average valence of said at least one silver-containing compound is at least 1.5.

5. The formulation of claim 1, the formulation containing less than 5% of a whitening agent.

6. The formulation of claim 1, the formulation containing less than 4% of silver-containing compounds selected from the group consisting of silver(II) fluoride ($AgF_2$), silver(II) picolinate ($C_{12}H_8AgN_2O_4$), silver(I) oxide and silver(II) oxide.

7. The formulation of claim 1, the formulation containing at least one carboxylic acid, said at least one carboxylic acid including a corresponding carboxylic acid of said aliphatic silver carboxylate having said nominal valence of 2, a molar ratio of said corresponding carboxylic acid to said aliphatic silver carboxylate having said nominal valence of at least 2 being at least 0.2.

8. The formulation of claim 1, wherein a backbone structure of said aliphatic silver carboxylate includes a straight hydrocarbon chain structure.

9. The formulation of claim 1, wherein said aliphatic silver carboxylate includes silver(II) phenylbutyrate.

10. The formulation of claim 1, said aliphatic silver carboxylate including a silver carboxylate of a fatty acid.

11. The formulation of claim 1, the formulation containing said aliphatic silver carboxylate in a range of 0.30% to 3.5%, by weight.

12. The formulation of claim 1, wherein a backbone structure of said aliphatic silver carboxylate includes a branched hydrocarbon chain structure.

13. The formulation of claim 1, wherein the hydrocarbon structure of said aliphatic silver carboxylate is a fully saturated structure.

14. The formulation of claim 1, wherein the hydrocarbon structure of said aliphatic silver carboxylate is a monounsaturated structure.

15. The formulation of claim 1, wherein the hydrocarbon structure of said aliphatic silver carboxylate is a polyunsaturated structure.

16. The formulation of claim 1, the formulation having a form of a cream.

17. The formulation of claim 1, the formulation having a form of an emulsion.

18. The formulation of claim 1, the formulation having a form of an ointment.

19. The formulation of claim 1, wherein said formulation is suitable for topical application to skin tissue.

20. The formulation of claim 1, wherein a content of said aliphatic silver carboxylate is within a range of 0.1% to 1.7%, on an $Ag_4O_4$ weight basis, the formulation having a standard whiteness value of at least 3.6, reflective units (RU).

21. The formulation of claim 20, wherein at least one of said aliphatic silver carboxylate and said carrier base selected, such that after standard ultraviolet light (UV) treatment, in which the formulation is subjected to constant exposure to UV for 12 hours at 240 nm, said standard whiteness value of the formulation remains within 0.6 RU of an initial whiteness value of the formulation prior to said treatment.

22. The formulation of claim 21, the formulation containing said aliphatic silver carboxylate in a range of 0.30% to 3.5%, by weight.

23. The formulation of claim 1, wherein the total silver content of the formulation is within the range of 0.05% to 3.5%, by weight.

24. The formulation of claim 23, wherein said total silver content of said at least one silver-containing compound is within a range of 0.09% to 1.7%, on an $Ag_4O_4$ weight basis, the formulation having a standard whiteness value of at least 4.1 reflective units (RU).

25. The formulation of claim 23, wherein said total silver content of said at least one silver-containing compound is within a range of 0.8% to 3.4%, by weight, the formulation having a standard whiteness value of at least 3.6 reflective units (RU).

* * * * *